(12) United States Patent
Gillet et al.

(10) Patent No.: US 11,866,712 B2
(45) Date of Patent: Jan. 9, 2024

(54) SYSTEM BASED ON THE REASSEMBLY OF GFP FOR STUDYING THE TRANS-TRANSLATIONAL ACTIVITY AND IDENTIFYING NEW ANTIBIOTICS

(71) Applicants: UNIVERSITE DE RENNES 1, Rennes (FR); CENTRE NATIONAL DE LA RECHERCHE SCIENTIFIQUE—CNRS—, Paris (FR)

(72) Inventors: Reynald Gillet, Le Verger (FR); Charlotte Guyomar, Porspoder (FR)

(73) Assignees: UNIVERSITE DE RENNES 1, Rennes (FR); CENTRE NATIONALE DE LA RECHERCHE SCIENTIFIQUE—CNRS, Paris (FR)

( * ) Notice: Subject to any disclaimer, the term of this patent is extended or adjusted under 35 U.S.C. 154(b) by 346 days.

(21) Appl. No.: 17/056,574

(22) PCT Filed: May 25, 2018

(86) PCT No.: PCT/EP2018/063780
§ 371 (c)(1),
(2) Date: Nov. 18, 2020

(87) PCT Pub. No.: WO2019/223879
PCT Pub. Date: Nov. 28, 2019

(65) Prior Publication Data
US 2021/0207151 A1    Jul. 8, 2021

(51) Int. Cl.
| | |
|---|---|
| *C12N 15/70* | (2006.01) |
| *G01N 33/58* | (2006.01) |
| *C12N 15/74* | (2006.01) |
| *C12N 15/78* | (2006.01) |
| *C12Q 1/02* | (2006.01) |
| *C12Q 1/18* | (2006.01) |
| *G01N 21/64* | (2006.01) |

(52) U.S. Cl.
CPC ............. *C12N 15/70* (2013.01); *C12N 15/74* (2013.01); *C12N 15/746* (2013.01); *C12N 15/78* (2013.01); *C12Q 1/025* (2013.01); *C12Q 1/18* (2013.01); *G01N 21/6486* (2013.01)

(58) Field of Classification Search
None
See application file for complete search history.

(56) References Cited

PUBLICATIONS

Cabantous et al: "In vivo and in vitro protein solubility assays using split GFP", Nature Methods, vol. 3, No. 10, pp. 845-854, Oct. 1, 2006.
Cheng: "Role of the TMRNA Pathway in Bacterial Physiology and Its Use in Antibiotic Development", Thesis in Genetics, Jan. 1, 2008.
Engelenburg et al: "Imaging type-III secretion reveals dynamics and spatial segregation of Salmonella effectors" Nature Methods, vol. 7, No. 4, pp. 325-350, Apr. 1, 2010.
Mace et al: "A Genetic Tool to Quantify trans-Translation Activity in Vivo", Journal of Molecular Biology, vol. 429, No. 23, pp. 3617-3625, Oct. 13, 2017.
Ozawa et al: "Designing split reporter proteins for analytical tools", Analytica Chimica Acta, vol. 556, No. 1, pp. 58-68, Jan. 18, 2006.
Ramadosa et al: "Small molecule inhibitors of trans-translation have broad-spectrum antibiotic activity", PNAS, vol. 110, No. 25, pp. 10282-10287, Jun. 18, 2013.

*Primary Examiner* — Jennifer E Graser
(74) *Attorney, Agent, or Firm* — WCF IP

(57) ABSTRACT

The present invention relates to a reporter system for trans-translation based on the reassembly of GFP and on the capacity of tmRNA to add a peptide tag to a protein blocked on a ribosome. The invention also relates to the in vivo or in vitro use of this reporter system for studying trans-translational activity and for identifying compounds capable of inhibiting trans-translation and therefore capable of being of interest as antibiotics.

Figure 1:
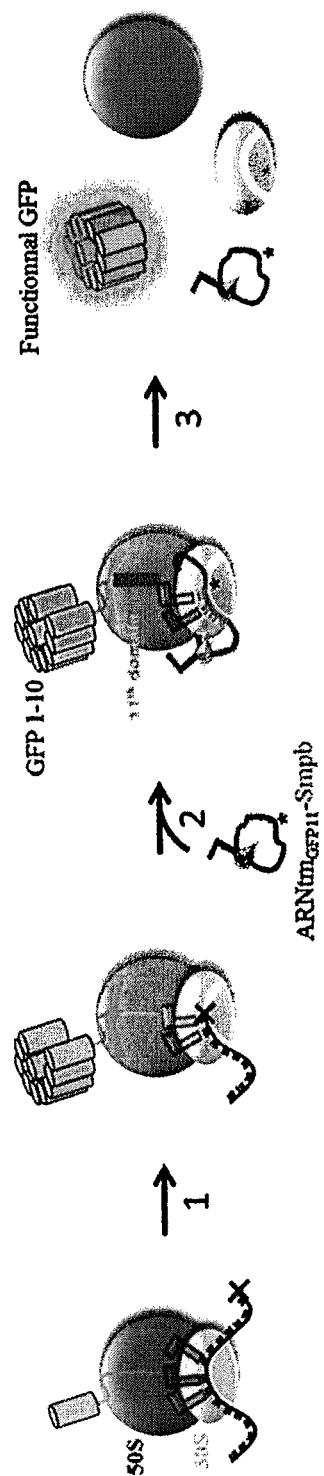

28 Claims, 3 Drawing Sheets
Specification includes a Sequence Listing.

SYSTEM BASED ON THE REASSEMBLY OF GFP FOR STUDYING THE TRANS-TRANSLATIONAL ACTIVITY AND IDENTIFYING NEW ANTIBIOTICS

CONTEXT OF THE INVENTION

Antibiotics are molecules which make it possible to specifically attack bacteria, by inhibiting their growth (bacteriostatic action) or by destroying them (bactericidal action). The appearance of antibiotics in the therapeutic arsenal began during the Second World War, shortly after the discovery and production of penicillin. This discovery, which is considered to be one of the major advances of the $XX^{th}$ century, rapidly led to the development of new medicaments for treating numerous deadly bacterial diseases such as tuberculosis, pneumonia, syphilis and tetanus, extending life expectancy by more than ten years.

However, the intensive use of antibiotics has introduced a selection pressure resulting in the worrying development of antibiotic-resistant microorganism populations and in a general decrease in therapeutic efficacy. It has been known for a long time that antibiotic resistance is a natural phenomenon—natural antibiotics and also resistance to these antibiotics go back more than 40 million years (D'Costa et al., Nature, 2011, 477: 457-461)—but the misconduct of antibacterial treatments, both in human medicine and in veterinary medicine, has greatly accelerated this phenomenon. Isolated at the beginning, these resistances have become massive and worrying. Some bacterial strains have become multiresistant, that is to say resistant to several antibiotics, and other strains have become toto-resistant, that is to say resistant to all available antibiotics. The latter case is fortunately still rare, but the phenomenon is increasing. It places physicians in a therapeutic impasse.

According to the World Health Organization (WHO), antibiotic resistance today constitutes "one of the most serious threats weighing on world health". In fact, numerous infections, such as pneumonia, tuberculosis and gonorrhea, have become more difficult to treat in the face of the loss of efficacy of the antibiotics used to combat them. Antibiotic resistance is responsible for prolonged hospitalizations and causes an increase in medical expenditure and in mortality. In the European Union alone, it is estimated that pharmaco-resistant bacteria are responsible each year for 25 000 deaths, with costs amounting to more than 1.5 billion US dollars in terms of health costs and losses of productivity (www.who.int/mediacentre/factsheets/antibiotic-resistance/fr/#-November 2015). The WHO talks about a "post-antibiotic era, in which common infections and minor injuries, which it has been possible to treat for decades, can once again kill". Plans of action are increasing in number, both at international level and within countries, in order to solve this problem with the aim of maintaining the efficacy of available antibiotics for as long as possible (for example by informing and educating health professionals and the population, by reducing antibiotic consumption and by optimizing the use of these medicaments). Another approach is to redynamize the development of new antibiotics, in particular against the most dangerous forms of resistant bacteria. As underlined by the WHO, over the course of 30 years, only two new families of antibiotics have come to light, while it is essential to have available new antibiotic molecules with original mechanisms of action.

The mechanism of the quality control of protein synthesis called trans-translation, which is the subject of one of the research programs of the team of the present Inventors, is particularly attractive for the development of new broad-spectrum antibiotics. Indeed, the translation of the genetic code into proteins via the ribosome is the basis of life for all cells. In light of the amount of biological data to be processed, it regularly occurs that the ribosome stalls and thus threatens the survival of the cell. In bacteria, the main mechanism for rescuing stalled ribosomes is trans-translation, borne by a hybrid ribonucleic acid (RNA): transfer-messenger RNA (tmRNA). Surprisingly, this system is essential to the survival of numerous pathogenic bacteria (*Staphylococcus aureus, Mycobacterium tuberculosis, Neisseria gonorrhoeae, Helicobacter pylori*, and *Shigella flexneri*) and is required for the virulence of other species (*Salmonella, Yersinia*, and *Francisella*). The structural and biological knowledge acquired during the past decade made it possible to identify trans-translation as a particularly attractive antibiotic target since it is absent in eukaryotic cells (Himeno et al., Front Genet., 2014, 5: 66, doi: 10.3389/fgene.2014.00066; Giudice et al., Front Microbiol., 2014, 5: 113, doi: 10.3389/fmicb.2014.00113). tmRNA and its partners, in particular small protein B (SmpB—Small Protein B) appear to be attractive targets for a new class of antibiotic molecules.

Despite some recent progress (Ramadoss et al., P.N.A.S USA, 2016, 110: 10282-10287), one thing curbing the development of such antibiotic molecules is the lack of simple and rapid methods for evaluating the effects of test compounds on trans-translation. There is therefore still, in the art, a need to have available new tools for studying trans-translational activity in various bacteria.

SUMMARY OF THE INVENTION

In general, the invention makes it possible to specifically detect the trans-translational activity by means of a rapid, simple, reliable and economical reporting system. More specifically, as indicated above, trans-translation, ensured by the tmRNA and the SmpB protein, is a mechanism for rescuing blocked ribosomes during bacterial translation. During this process, the tmRNA adds a proteolysis tag to the incomplete protein blocked in the ribosome, thereby enabling rapid degradation of the tagged protein by proteases. In order to measure the trans-translational activity, the reporter system of the present invention uses, on the one hand, the capacity for addition, by the tmRNA, of a proteolysis tag to the incomplete peptide blocked in the ribosome, and on the other hand, the reassembly of green fluorescent protein, GFP, the isolated fragments of which are not fluorescent. The reporter system according to the invention is suitable for use in vivo (that is to say in a medium containing the bacterium itself) under various culture conditions (agar or liquid cultures). Even more advantageously, in particular in the case of bacteria which are highly pathogenic to human beings, the reporter system according to the invention is also suitable for use in vitro (that is to say in cell-free medium or medium not containing the bacterium). Furthermore, contrary to the already existing methods which are applicable only to *Escherichia coli*, the system according to the invention is such that it is readily transposable in various bacterial species and strains. The result can be visualized by means of a large variety of fluorescence measurement techniques (fluorescence microscopy, fluorimetry, etc.). The system has also been optimized for reading on a multiwell plate so as to facilitate the screening of active compounds. Indeed, a reporter system according to the invention is of use not only as an essential tool in fundamental research on trans-translation, but also in the screening of compounds with a view to identifying new antibiotics.

Consequently, in a first aspect, the present invention relates to a reporter system for the trans-translational activity of a bacterial species, comprising:
- a nucleotide sequence encoding the first 10 domains of GFP and not comprising a stop codon;
- the SmpB protein of said bacterial species, or a biologically active fragment of said protein, or a DNA sequence encoding said protein or said fragment; and
- a modified tmRNA, wherein the modified tmRNA is the tmRNA of said bacterial species, in which the portion of sequence encoding the proteolysis tag is replaced with a sequence encoding the 11$^{th}$ domain of GFP, or a DNA sequence encoding said modified tmRNA.

In certain embodiments, the bacterial species is a Gram-positive (Gram+) bacterium, a Gram-negative (Gram−) bacterium, or a mycobacterium.

In certain embodiments, the reporter system of the invention is characterized in that the GFP is Superfolder GFP.

In certain embodiments, the nucleotide sequence encoding the first 10 domains of GFP and not comprising a stop codon is a DNA sequence of which the transcription produces an mRNA encoding the first 10 domains of GFP and not comprising a stop codon.

In certain embodiments, the nucleotide sequence encoding the first 10 domains of GFP and not comprising a stop codon is functionally linked in the 3' position, to the sequence of a strong terminator (for in vivo use). The strong terminator may be a succession of rare codons, a ribonuclease recognition sequence, a ribosome-blocking sequence, or a terminator comprising at least one stem-loop structure.

In certain embodiments, the nucleotide sequence encoding the first 10 domains of GFP and not comprising a stop codon is functionally linked, in the 5' position, to a translation initiation site corresponding to a ribosome-binding site and to a promoter, in particular the T7 promoter.

In certain embodiments, the nucleotide sequence encoding the first 10 domains of GFP and not comprising a stop codon and functionally linked, in the 5' position, to a translation initiation site corresponding to an RBS ribosome-binding site and to the T7 promoter consists of the sequence SEQ ID NO: 1.

In certain embodiments, the reporter system is characterized in that:
- the bacterial species is *Escherichia coli* and the DNA sequence encoding the SmpB protein is the sequence SEQ ID NO: 2 or any variant encoding the SmpB protein of *Escherichia coli*;
- the bacterial species is *Enterococcus faecium* and the DNA sequence encoding the SmpB protein is the sequence SEQ ID NO: 3 or any variant encoding the SmpB protein of *Enterococcus faecium*;
- the bacterial species is *Staphylococcus aureus* and the DNA sequence encoding the SmpB protein is the sequence SEQ ID NO: 4 or any variant encoding the SmpB protein of *Staphylococcus aureus*;
- the bacterial species is *Klebsiella pneumoniae* and the DNA sequence encoding the SmpB protein is the sequence SEQ ID NO: 5 or any variant encoding the SmpB protein of *Klebsiella pneumoniae*;
- the bacterial species is *Acinetobacter baumannii* and the DNA sequence encoding the SmpB protein is the sequence SEQ ID NO: 6 or any variant encoding the SmpB protein of *Acinetobacter baumannii*;
- the bacterial species is *Pseudomonas aeruginosa* and the DNA sequence encoding the SmpB protein is the sequence SEQ ID NO: 7 or any variant encoding the SmpB protein of *Pseudomonas aeruginosa*;
- the bacterial species is *Enterobacter cloacae* and the DNA sequence encoding the SmpB protein is the sequence SEQ ID NO: 8 or any variant encoding the SmpB protein of *Enterobacter cloacae*; or
- the bacterial species is *Mycobacterium tuberculosis* and the DNA sequence encoding the SmpB protein is the sequence SEQ ID NO: 9 or any variant encoding the SmpB protein of *Mycobacterium tuberculosis*.

In certain embodiments, the sequence encoding the 11$^{th}$ domain of GFP is a DNA sequence consisting of the sequence SEQ ID NO: 19 or any variant which encodes the sequence SEQ ID NO: 18 (ARDHMVLHEYVNAAGIT).

In certain embodiments, the modified tmRNA is also modified such that the sequence in the 3' position of the sequence encoding the 11$^{th}$ domain of GFP is replaced with a sequence which pairs with a region of the sequence encoding the 11$^{th}$ domain of GFP so as to form a helix. For example, the sequence encoding the 11$^{th}$ domain of GFP is a DNA sequence consisting of the sequence SEQ ID NO: 19 or any variant which encodes the sequence SEQ ID NO: 18 (ARDHMVLHEYVNAAGIT) and the sequence which pairs with a region of the sequence encoding the 11$^{th}$ domain of GFP so as to form a helix is a DNA sequence consisting of the sequence SEQ ID NO: 20.

Thus, in certain embodiments, such a reporter system is characterized in that:
- the bacterial species is *Escherichia coli* and the DNA sequence encoding the modified tmRNA is the sequence SEQ ID NO: 21;
- the bacterial species is *Enterococcus faecium* and the DNA sequence encoding the modified tmRNA is the sequence SEQ ID NO: 22;
- the bacterial species is *Staphylococcus aureus* and the DNA sequence encoding the modified tmRNA is the sequence SEQ ID NO: 23;
- the bacterial species is *Klebsiella pneumoniae* and the DNA sequence encoding the modified tmRNA is the sequence SEQ ID NO: 24;
- the bacterial species is *Acinetobacter baumannii* and the DNA sequence encoding the modified tmRNA is the sequence SEQ ID NO: 25;
- the bacterial species is *Pseudomonas aeruginosa* and the DNA sequence encoding the modified tmRNA is the sequence SEQ ID NO: 26;
- the bacterial species is *Enterobacter cloacae* and the DNA sequence encoding the modified tmRNA is the sequence SEQ ID NO: 27; or
- the bacterial species is *Mycobacterium tuberculosis* and the DNA sequence encoding the modified tmRNA is the sequence SEQ ID NO: 28.

In certain embodiments, at least one of the following sequences: the nucleotide sequence encoding the first 10 domains of GFP and not comprising a stop codon; the DNA sequence encoding the SmpB protein or a biologically active fragment of said SmpB protein; and the DNA sequence encoding the modified tmRNA, is inserted into a plasmid.

In certain embodiments, the nucleotide sequence encoding the first 10 domains of GFP and not comprising a stop codon; the DNA sequence encoding the SmpB protein or a biologically active fragment of said Smp protein; and the DNA sequence encoding the modified tmRNA, are inserted into one or more plasmids.

In certain embodiments, the reporter system according to the invention also comprises:

an anti-tmRNA oligonucleotide which comprises, or consists of, a DNA sequence complementary to the DNA sequence encoding the proteolysis tag of the tmRNA of the bacterial species of the bacterial system for protein synthesis with which the reporter system is intended to be used.

In another aspect, the invention relates to the use of a reporter system, as described herein, for studying the trans-translational activity of a bacterial species.

In yet another aspect, the invention relates to the use of a reporter system, as described herein, for identifying, in particular by screening, compounds capable of inhibiting bacterial trans-translation.

In yet another aspect, the invention relates to a method for screening for compounds capable of inhibiting bacterial trans-translation, comprising steps consisting in:
  (a) incubating a bacterial system for protein synthesis with a test compound;
  (b) adding, to the bacterial system for protein synthesis incubated with the test compound, a reporter system for trans-translation as described herein; and
  (c) identifying the effect of the test compound on trans-translation by detecting and/or by measuring GFP fluorescence.

In certain embodiments, the screening method also comprises: a step consisting in:
  (d) comparing the measurement of the fluorescence measured in step (c) with the measurement of the fluorescence measured under the same conditions in the absence of the test compound.

In certain embodiments, the screening method is characterized in that the test compound is identified as a compound capable of inhibiting bacterial trans-translation if the fluorescence measured in step (d) is greater than the fluorescence measured in step (c).

In certain embodiments, the bacterial system for protein synthesis used in the screening method is from the same bacterial species as the bacterial species of the reporter system for trans-translational activity.

In other embodiments, the bacterial system for protein synthesis used in the screening method is from a bacterial species different than the bacterial species of the reporter system for trans-translational activity.

In certain embodiments, the bacterial system for protein synthesis is an in vitro system. For example, the in vitro bacterial system for protein synthesis can be a reconstituted cell-free protein synthesis system. The reconstituted cell-free protein synthesis system can comprise:
  a bacterial ribosome,
  tRNAs of the bacterial species,
  elements required for transcription by the bacterial ribosome,
  elements required for translation by the bacterial ribosome,
  an energy-regenerating system, and
  buffers, and salts.

In other embodiments, the bacterial system for protein synthesis is an in vivo system. For example, the in vivo bacterial system for protein synthesis can be a bacterial cell. For example, the screening method can be characterized in that (1) the in vivo bacterial system for protein synthesis is a host bacterial cell comprising, integrated into its genome (in the form of a plasmid), the DNA sequence encoding the SmpB protein and the DNA sequence encoding the modified tmRNA and (2) in step (b), only the nucleotide sequence encoding the first 10 domains of GFP and not comprising a stop codon is added to the host bacterial cell.

In yet another aspect, the invention relates to a kit comprising a reporter system for the trans-translational activity of a bacterial species as described herein.

In certain embodiments, the kit also comprises instructions for carrying out a screening method according to the invention.

In certain embodiments, the kit also comprises a bacterial system for protein synthesis as described herein.

A more detailed description of certain preferred embodiments of the invention is given below.

FIGURE LEGENDS

FIG. 1: Diagram of a test for trans-translation of the truncated green fluorescent protein (GFP) by the modified tmRNA. Step 1: The canonical translation of the mRNA of sfGFP1-10 (dark) is stopped by the absence of stop codon (red cross), which causes blocking of the ribosome. Two tRNAs are in the ribosome binding site P (yellow) and ribosome binding site E (violet). The binding site A is empty. Step 2: The tmRNA$_{GFP11}$-SmpB (red and blue, respectively) complex binds to the blocked ribosome. The C-terminal portion of SmpB recognizes the empty binding side A. The canonical translation begins again by virtue of the messenger domain of the tmRNA$_{GFP11}$ encoding the $11^{th}$ domain missing from the sfGFP (green portion of the tmRNA). Consequently, the $11^{th}$ domain is added to the incomplete sfGFP1-10. Step 3: The end of the process takes place when the stop codon of the tmRNA (red star) is reached. The complete sfGFP is released and becomes fluorescent. The 50S (in blue) and 30S (in yellow) subunits of the ribosome are dissociated in order to be reused, and the tmRNA$_{GFP11}$-SmpB complex is also recycled.

Figure 2:
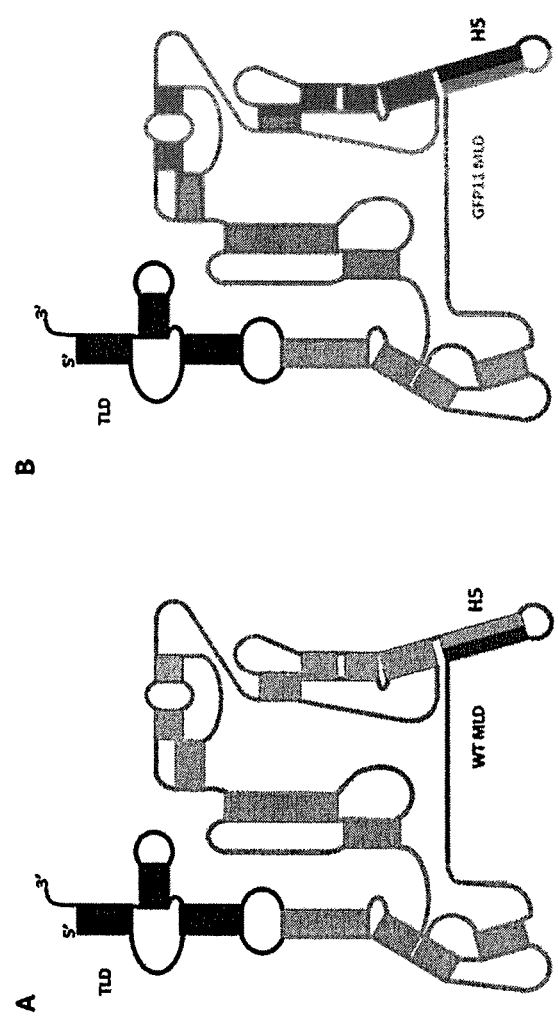

FIG. 2: Diagram of the secondary structures of the wild-type tmRNA and of the modified tmRNA$_{GFP11}$. (A) Secondary structure of the wild-type Escherichia coli tmRNA. The TLD domain (transfer-like domain) is represented in black and the wild-type MLD domain (messenger-like domain) is represented in blue (this domain encodes the peptide tag specifically recognized by trans-translation-specific proteases. (B) tmRNA$_{GFP11}$ modified according to the invention with a new domain of messenger type (GFP11 MLD) encoding the $11^{th}$ domain of GFP in green. The compensatory mutations which maintain the pairing interactions of the bases of the H5 helix are represented in dark green (H5*).

Figure 3:
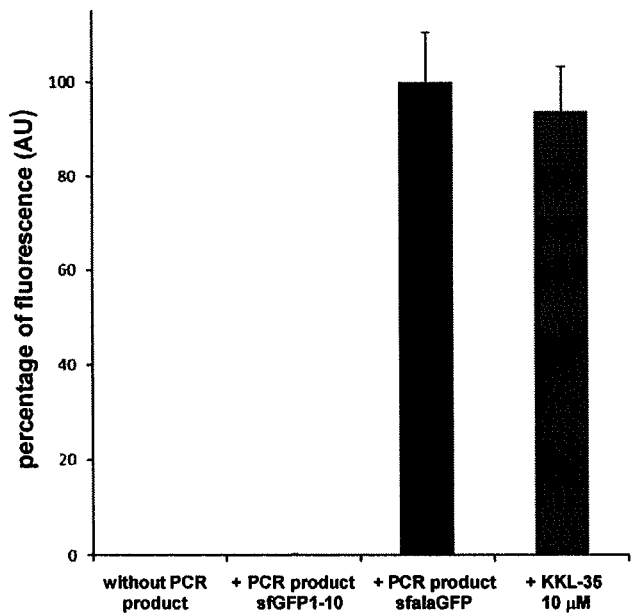
Figure 3:
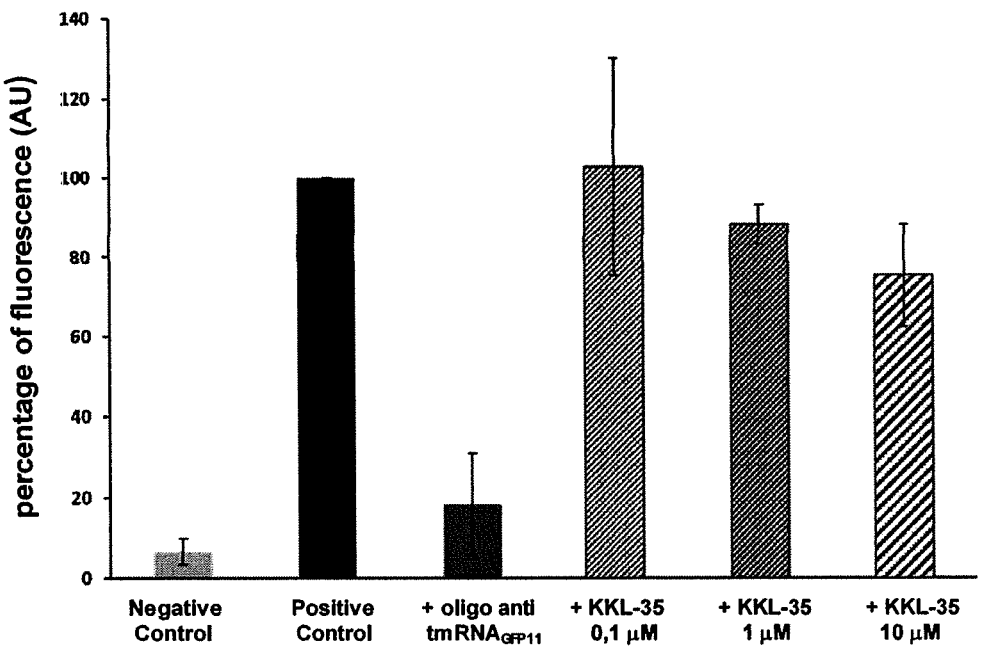

FIG. 3: Measurement of the trans-translation activity by fluorescence. The fluorescence signal was detected by a spectrofluorometer at 510 nm with excitation at 485 nm. (A) Fluorescence controls (three repetitions). In the absence of PCR products, no auto-fluorescence of the components of the kit is noted. The addition of the sfGFP1-10 PCR product ending with a stop codon makes it possible to verify the absence of fluorescence of the first 10 domains alone. The sfalaGFP PCR product makes it possible to verify the production of a fluorescent functional GFP when an alanine is added between domains 10 and 11. The addition of KKL-35 (10 µM) to the sfalaGFP PCR product confirms the absence of anti-transcription and anti-translation activity of the molecule. (B) Influence of the anti-tmRNA$_{GFP11}$ antisense oligonucleotide and KKL-35 on the in vitro trans-translation. The negative control does not contain tmRNA$_{GFP11}$ contrary to the positive control. The two tmRNA$_{GFP11}$ purified in vivo or in vitro were tested and were functional. The antisense oligonucleotide was added at a final concentration of 5 µM. Serial dilutions of KKL-35 were tested (final concentration of 0.1, 1 and 10 µM, for at least three independent experiments).

DETAILED DESCRIPTION OF THE INVENTION

As mentioned above, the present invention relates to a system which makes it possible to study the trans-translational activity of a bacterium both in vivo and in vitro. This system, which is transposable to various bacterial species, in particular has a use in screening for compounds capable of inhibiting trans-translation and therefore capable of being of interest as antibiotics.

I—Reporter System for Trans-Translational Activity

A reporter system for the trans-translational activity of a bacterial species according to the invention is based on the reassembly of green fluorescent protein, GFP, and on the capacity of the bacterial transfer-messenger RNA (tmRNA) to add a peptide tag to a polypeptide blocked on a ribosome. Thus, more specifically, a system according to the invention contains three main components:
- a nucleotide sequence encoding the first 10 domains of GFP and not comprising a stop codon;
- the SmpB protein of said bacterial species, or a biological active fragment of this protein, or a DNA sequence encoding this protein or this fragment; and
- the tmRNA of said bacterial species in which the portion of sequence encoding the proteolysis tag is replaced with a sequence encoding the 11$^{th}$ domain GFP, or a DNA sequence encoding this modified tmRNA.

A. The Trans-Translation

Translation is the process by which the genetic information contained in messenger RNA (mRNA) sequences is decoded into proteins by a central molecular machine: the ribosome. This mechanism involves not only the ribosome, but also additional protein factors and transfer RNAs (tRNAs) which act as linkers between the mRNA and the amino acids which are integrated into the growing polypeptide. During the translation, the ribosomes translate the messenger and synthesize the growing polypeptide until a stop codon on the mRNA is encountered.

However, the ribosomes regularly stall at the 3' end of an mRNA, in particular because of the accidental absence of a stop codon. In bacteria, the main quality control mechanism which makes it possible to release blocked ribosomes is trans-translation (Guidice et al., Front. Microbiol., 2014, 5; Himeno et al., Front. Genet., 2014, 5). The trans-translation is borne by a particular RNA: the transfer-messenger RNA (tmRNA), associated with the small protein, SmpB (small protein B) (Karzai et al., EMBO J., 1999, 18(13): 3793-3799). The tmRNA is a hybrid molecule which has the properties both of a transfer RNA and of a messenger RNA (Muto et al., Trends Biochem. Sci., 1998, 23(1): 25-29). The tmRNA is encoded by the ssrA gene and is always amino-acylated by an alanine. It has two important domains: the TLD domain (t-RNA-like domain) and the MLD domain (mRNA-like domain). When the ribosomes reach non-stop mRNAs, the ribosome decoding site becomes vacant. The TLD domain of the tmRNA binds to the SmpB protein in order to maintain its three-dimensional conformation and to mimic a canonical tRNA. The tmRNA-SmpB complex thus formed, in combination with the EF-Tu elongation factor, recognizes the blocked ribosome by virtue of SmpB which inserts and structures its C-terminal portion as a function of the presence or absence of an mRNA in the ribosome reading channel (Neubauer et al., Science, 2012, 355: 1366-1369). The MLD domain of the tmRNA, correctly positioned by virtue of SmpB (Weis et al., EMBO J., 2010, 29: 3810-3818; Weis et al., RNA, 2010, 16: 299-306), is then immediately translated. The MLD domain of the tmRNA, which makes it possible to reinitiate the translational process, encodes a signal consisting of a peptide tag specifically recognized by trans-translation-specific proteases; this signal is followed by a stop codon. The addition of the proteolysis tag to the incomplete polypeptide previously blocked on the ribosome allows the degradation of the polypeptide after its release. The ribosomes are then recycled, while the problematic non-stop mRNA is degraded by RNase R (Richards et al., Mol. Microbiol., 2006, 62(6): 1700-1712; Domingues et al., Biochimie, 2015, 114 (Supplement C): 113-118).

B. Principle of the Invention Based on the Reassembly of GFP

As already indicated, the system according to the invention is based on the reassembly of green fluorescent protein, GFP. Green fluorescent protein (or GFP) is an intrinsically fluorescent protein, derived from a jellyfish (*Aequorea victoria*). The non-modified GFP, termed wild-type GFP, consists of 238 amino acids for a molecular weight of approximately 27 kDa. It has two excitation maxima, the first at a wavelength of 395 nm (UV light) and the second at 475 nm (blue light). The maximum emission wavelength is at 504 nm. The polypeptide chain of GFP folds on itself—the various amino acids act like magnets, approach one another and form a compact three-dimensional structure containing a β-barrel composed of 11 β-sheets and of one α-helix which is at the core of the β-barrel. The α-helix contains, in its peptide sequence, the three amino acids which constitute the chromophore of GFP, namely the residues Ser65, Tyr66 and Gly67 (Serine, Tyrosine and Glycine). The term "GFP", as used herein, denotes the green fluorescent protein derived from the jellyfish *Aequorea victoria* or a variant having a desired property. Thus, for example, the GFP may be the GFP called "Superfolder GFP" (or "sfGFP") which was generated by mutation and which has improved folding properties (speed and efficiency) compared with the wild-type GFP (Pedelacq et al., Nature Biotechnol., 2006, 24(1): 79-88).

The GFP molecule is fluorescent only when it contains all of the 11 β-sheets (or 11 domains). Thus, whereas the complex derived from the reassembly between two fragments of GFP is fluorescent, the isolated two GFP fragments are not (or only very weakly) fluorescent (Kent et al., J. Am. Chem. Soc., 2008, 130: 9664-9665; Kent et al., J. Am. Chem. Soc., 2009, 131: 15988-15989; Cabantous et al., Nature Biotechnology, 2005, 23(1): 102-107; Pedelacq et al., Nature Biotechn., 2006, 24(1): 79-88; Cabantous et al., Nature Methods, 2006, 3(10): 845-854; Kamiyama et al., Nature Commun., 2016, 7, 11046; Miller et al., J. Mol. Biol., 2015, 427(11): 2039-2055). It is this property which is exploited in the reporter system for trans-translational activity according to the invention.

More specifically, as represented in the diagram of FIG. 1, in a test according to the invention, the nucleotide sequence encoding the first 10 domains of GFP and not comprising a stop codon is translated by a ribosome without the protein thus produced being released, thereby creating a situation where the ribosome is stalled. The incomplete protein thus generated contains the first 10 domains of GFP and is therefore non-fluorescent. The SmpB and tmRNA molecules activate the trans-translation mechanism, which, if it is active, results in the addition of the proteolysis tag to the incomplete protein blocked in the ribosome. However, in the modified tmRNA of the system according to the invention, the sequence encoding the proteolysis tag is replaced with a sequence encoding the $11^{th}$ domain of GFP. The trans-translation reaction therefore adds, to the blocked protein containing the first 10 domains of GFP, the $11^{th}$ domain of GFP, thereby generating and releasing a complete GFP molecule—that is to say a molecule which is fluorescent. The detection (and/or the measurement) of the fluorescence makes it possible to reach a conclusion as to the activity of the trans-translation system. When the trans-translation mechanism is inactive or damaged or else inhibited (for example by the presence of a compound which has an anti-trans-translation activity), there is no (or little) addition of the $11^{th}$ domain of GFP, and therefore no (or little) formation of complete GFP, which leads to an absence or a weak intensity of fluorescence.

As those skilled in the art will recognize, for reasons of retaining three-dimensional structure, the choice was made herein to reassemble the $11^{th}$ domain of GFP with the first 10 domains; however, other variants can be envisioned. Thus, it is also possible to develop a system according to the invention wherein the nucleotide sequence encodes the first nine or eight domains of GFP and wherein the tmRNA is modified such that the portion of sequence encoding the proteolysis tag is replaced with a sequence encoding the $10^{th}$ and $11^{th}$ domains of GFP or encoding the $9^{th}$, $10^{th}$ and $11^{th}$ domains of GFP, respectively. Such variants of the system are also part of the subjects of the invention.

Furthermore, there are at the current time numerous GFP-derived fluorescent proteins obtained by mutagenesis approaches, which have made it possible to introduce substitutions at the level of the chromophore and/or of a portion of sequence distant from the chromophore and thus to modify the spectral properties of the protein. The derived fluorescent proteins also have a β-barrel structure composed of 11 β-sheets and of an α-helix which is at the core of the β-barrel. Since the beginning of the 2000s, numerous variants have been obtained from GFP, most covering the blue-to-yellow emission spectrum (that is to say from 420 to 550 nm). This includes the fluorescent proteins which emit in the blue range (called BFPs or Blue Fluorescent Proteins, which emit between 425 nm and 470 nm), in the cyan range (CFPs or Cyan Fluorescent Proteins, which emit between 471 nm and 500 nm), in the green range (GFPs or Green Fluorescent Proteins, which emit between 501 nm and 520 nm), and in the yellow range (YFPs or Yellow Fluorescent Proteins, which emit between 521 nm and 550 nm). Mention may in particular be made of the variants called: EGFP (E for enhanced), which fluoresce in the green range; EBFP, which fluoresce in the blue range; ECFP, which fluoresce in the cyan range; and EYFP, which fluoresces in the yellow range. Thus, in a system according to the invention, it is conceivable to use such a GFP derivative in place of the GFP. Such variants of the system are also part of the subjects of the invention.

Finally, knowing that the β-barrel structure is conserved in all the fluorescent proteins discovered to date in organisms other than the *Aequorea victoria* jellyfish, it is also possible to envision using one of these fluorescent proteins, or a variant thereof, in place of the GFP.

Throughout the subsequent text, in order to facilitate understanding, the system according to the invention is described using GFP and the reassembly of the first 10 domains of GFP with the $11^{th}$ domain by addition of a tag by a modified tmRNA.

C. Nucleotide Sequence Encoding the First 10 Domains of GFP and not Comprising a Stop Codon The terms "nucleotide sequence", "nucleic acid", "nucleic sequence", "polynucleotide" and "oligonucleotide" are used herein without implied distinction. These terms are intended to denote a precise series of modified or non-modified nucleotides, making it possible to define a region of a nucleic acid, and able to correspond both to a double-stranded DNA or a single-stranded DNA and also to products of transcription of these DNAs.

In certain embodiments, the nucleotide sequence is a messenger RNA (mRNA) encoding the first 10 domains of GFP and not comprising a stop codon. However, mRNAs are fragile and easily degradable molecules that it is difficult, at the current time, to store. Thus, in certain preferred embodiments, the nucleotide sequence is a DNA of which the transcription produces an mRNA encoding the first 10 domains of GFP and not comprising a stop codon. The transcription of the DNA into messenger RNA (mRNA) is then carried out in situ (that is to say during the test of the invention). The DNA may be a single-stranded or double-stranded DNA. In certain preferred embodiments, the DNA is a double-stranded DNA, which may be a naked DNA or a plasma DNA (that is to say a DNA inserted into a plasmid—see below).

Sequence encoding the first 10 domains of GFP. The terms "first 10 domains of GFP" and "$11^{th}$ domain of GFP" denote, respectively, the ten β-domains which are in the N-terminal portion of GFP and the β-domain which is in the C-terminal portion of GFP. More generally, the terms "first X domains of GFP" and "last Y domains of GFP" denote respectively, the X domains which are in the N-terminal portion of GFP and the Y domains which are in the C-terminal portion of GFP, wherein X and Y are each an integer and wherein X+Y=11. Generally, X=10 or 9 or 8 and Y=1 or 2 or 3, respectively.

The nucleotide and peptide sequences of GFP, which can be used in carrying out the present invention, are known in the art (Prasher et al., Gene, 1992, 111(2): 229-233; Inouye et al., FEBS Lett., 1994, 341(2-3): 277-280) and available in the databases (GenBank, EMBL Nucleotide Sequence Database, Swiss-Prot, UniProt, etc.). Mention may for example be made of the polypeptide sequences (GenBank Accession Nos.: AAA27722.1; AAA27721.1; AAA58246.1) and the mRNA sequences (GenBank Accession Nos.: L29345.1; M62654.1; M62653.1). The peptide sequence of Superfolder GFP is also known (PDB Accession No. 2B3P; Pedelacq et al., Nature Biotechnol., 2006, 24(1): 79-88). Likewise, the GFP domains have been identified (Ormö et al., Science, 1996, 273: 1392-1395; Yang et al., Nature Biotechnology, 1996, 14: 1246-1251).

Absence of stop codon and strong terminator. The terms "not comprising a stop codon" and "devoid of stop codon" are used herein interchangeably. They signify that the nucleotide sequence encoding the first 10 domains of GFPs stops in the 3' position exactly at the final codon of domain 10 in the in vitro system or is functionally linked, in the 3' position, to the sequence of a strong terminator. The terms "linked in a functional manner" and "functionally linked" are used without implied distinction and refer to a functional link between a regulatory sequence and the nucleic acid sequence which it controls. The terms "terminator" and "transcription terminator" are used herein without implied distinction. They denote a sequence which marks the end of the transcription of the gene or of an operon into messenger RNA. The term "strong terminator" denotes herein a terminator which stops transcription prematurely, and results in the synthesis of an mRNA devoid of a stop codon. Thus, in the implementation of the invention, the sequence encoding the first 10 domains of GFP does not contain a stop codon. In other words, the stop codon of this sequence is absent in the in vitro system or is replaced with the sequence of the strong terminator in vivo. In a system intended for use in vivo, the strong terminator is therefore placed at the end (that is to say downstream or 3') of the sequence encoding the first 10 domains of GFP so that the transcription stops without encountering a stop codon. As a result of this, the mRNA is blocked in the ribosome and the trans-translation process is induced.

In certain embodiments, the 3' sequence (or the strong terminator) can be a sequence which causes ribosome blocking, a site for cleavage by an RNAse (that is to say a ribonuclease recognition sequence), a succession of rare codons (which will cause the involvement of an RNase), or a terminator comprising at least one stem-loop structure. A stem-loop structure is a DNA sequence which folds so as to form a hairpin structure. Such a DNA sequence can, for example, consist of an inverted repeat sequence (having a strong delta G) followed by a series of thymines T (uracils U on the RNA transcribed). During its transcription into RNA, the inverted repeat sequence adopts a stem-loop structure which causes the RNA polymerase to pause. The transcribed RNA is then paired to the strand of template DNA only by the sequence of uridines which follows. These A-U interactions are weak, and the RNA synthesized can detach from its template. The transcription stops. The stem-loop structures are important in intrinsic transcription terminations (or rho-independent terminations) of procaryotes. Thus, the terminator with a stem-loop structure may be the natural intrinsic transcription terminator of a bacterium (in particular of the bacterial species of which it is desired to study the trans-transcription) or a chimeric terminator, or alternatively a combination of such terminators.

Construct or expression cassette. A nucleotide sequence encoding the first 10 domains of GFP and not comprising a stop codon can be inserted into a "construct" or "expression cassette" comprising elements which allow transcription and translation by a bacterial ribosome. Those skilled in the art know how to select such elements, including for example a translation initiation site and a promoter.

Thus, preferably, in a construct comprising the nucleotide sequence encoding the first 10 domains of GFP and not comprising a stop codon, the nucleotide sequence is functionally linked, in the 5' position, to the sequence of a promoter. The term "promoter" is intended to mean any polynucleotide capable of regulating the expression of a nucleotide sequence to which it is functionally linked. In the context of the invention, a promoter-type regulatory sequence is a regulatory region recognized by an RNA polymerase of the bacterial species of interest and capable of initiating the transcription of the sequence encoding the first 10 domains of GFP. The promoter may be homologous to the bacterial species or, alternatively, may be heterologous to the bacterial species. Furthermore, the promoter may be a natural sequence (that is to say a sequence which exists in nature) or a synthetic sequence (that is to say a sequence which does not exist as such in nature—for example a consensus sequence for a given bacterial species).

The promoters suitable for transcription by the RNA polymerase of bacterial species include, without limitation, in the particular case of the *E. coli* bacterium, the lac, lacUV5, tac, trc, trp, araBAD, phoA, recA, proU, cst-I, tetA, cadA, nar, pL, cspA, SP6, T7, T3, T5, T4, nprM, and VHb promoters. In certain preferred embodiments, the promoter is the T7 promoter. Consensus sequences of promoters suitable for transcription by the RNA polymerase of bacterial species are known in the art. For example, when the reporter system is intended to be used in *Escherichia coli* (*E. coli*), the consensus sequence may be that described by Kanaya and Kudo (Nucleic Acids Symp., 1991, 25: 41-42). The promoter is optionally associated with a regulator, the choice of the regulator being dependent on the bacterial species. Numerous examples of regulators have been described, the most conventional being the LacI and TetR proteins. In this eventuality, a suitable operator is associated with the promoter. Those skilled in the art know how to select the promoter and the associated regulator that are most suitable depending on the final use of the reporter genetic construct.

Consensus sequences of promoters suitable for bacterial transcription are known in the art. For example, when the reporter system is intended to be used in *Escherichia coli* (*E. coli*), the consensus sequence may be that described by Kanaya and Kudo (Nucleic Acids Symp., 1991, 25: 41-42).

Preferably, in a construct comprising the nucleotide sequence encoding the first 10 domains of GFP and not comprising a stop codon, the nucleotide sequence is functionally linked, in the 5' positon, to the sequence of a translation initiation site. The initiation site comprises a sequence corresponding to a ribosome binding site (SD or RBS), which allows the initiation of the protein synthesis (translation). The ribosome binding sites are complementary to the end of 16S RNA, are generally rich in purines (A and G) and have a length of from 3 to 9 consecutive nucleotides. Such sequences are known in the art. In the embodiments of the invention wherein the genetic construct is intended to be used in *E. coli*, the sequence corresponding to a ribosome binding site may be: AAGGAGA, which is a consensus sequence for *E. coli* (Barrick et al., Nucleic Acids Res., 1994, 22: 1287-1295). A sequence corresponding to a ribosome binding site is generally placed 6 to 12 nucleotides upstream of the gene start codon. An initiation site in a construct according to the invention therefore consists of a sequence corresponding to a ribosome binding site and of 6 to 12 additional nucleotides. In the embodiments of the invention wherein the genetic construct is intended to be used in *E. coli*, the additional 6 to 12 nucleotides may, for example, be: TATACAT—an arbitrary sequence.

Preparation of the nucleotide sequence encoding the first 10 domains of GFP and not comprising a stop codon. The polynucleotide sequences can be prepared by any appropriate method. The techniques for isolating or cloning a gene or a nucleotide sequence encoding a protein or a domain specific for a protein are known in the art and include isolation from genomic DNA, preparation from complementary DNA, or a combination of these methods. The cloning of a gene, or of a nucleotide sequence encoding a protein or a domain specific for a protein, from a genomic DNA can be carried out for example using a polymerase chain reaction (PCR) or by screening expression libraries in order to detect the cloned DNA fragments with identical structural characteristics (Innis et al., "PCR: A Guide to Method and Application", 1990, Academic Press: New York). It is also possible to use a chemical synthesis method for preparing a polynucleotide sequence. The methods for total chemical synthesis of DNA or RNA strands are known to those skilled in the art, and use automated commercial synthesizers.

The examples presented at the end of this document describe a method for preparing a nucleotide sequence encoding the first 10 domains of GFP and not comprising a stop codon (GFP1-10 nonstop) by PCR from a vector, pETGFP 1-10, which has been previously described (Cabantous et al., Nature Biotechnology, 2005, 23: 102-107; Cabantous and Waldo, Nature Methods, 2006, 3(10): 845-854; Kaddoum et al., Biotechniques, 2010, 49(4): 727-228). In this example, the nucleotide sequence encoding the first 10 domains of GFP and not comprising a stop codon is functionally linked, in a 5' position, to a T7 promoter, and to a translation initiation site corresponding to the RBS ribosome binding site, and has the following sequence SEQ ID NO: 1:

```
5' CTCGATCCCGCGAAATTAATACGACTCACTATAGGGGAATTGTGAGC

GGATAACAATTCCCCTCTAGAAATAATTTTGTTTAACTTTAAGAAGGAGA

TATACATATGGGTGGCACTAGTAGCAAAGGAGAAGAACTTTTCACTGGAG

TTGTCCCAATTCTTGTTGAATTAGATGGTGATGTTAATGGGCACAAATTT

TCTGTCAGAGGAGAGGGTGAAGGTGATGCTACAATCGGAAAACTCACCCT

TAAATTTATTTGCACTACTGGAAAACTACCTGTTCCATGGCCAACACTTG

TCACTACTCTGACCTATGGTGTTCAATGCTTTTCCCGTTATCCGGATCAC

ATGAAAAGGCATGACTTTTTCAAGAGTGCCATGCCCGAAGGTTATGTACA

GGAACGCACTATATCTTTCAAAGATGACGGGAAATACAAGACGCGTGCTG

TAGTCAAGTTTGAAGGTGATACCCTTGTTAATCGTATCGAGTTAAAGGGT

ACTGATTTTAAAGAAGATGGAAACATTCTCGGACACAAACTCGAGTACAA

CTTTAACTCACACAATGTATACATCACGGCAGACAAACAAAAGAATGGAA

TCAAAGCTAACTTCACAGTTCGCCACAACGTTGAAGATGGTTCCGTTCAA

CTAGCAGACCATTATCAACAAAATACTCCAATTGGCGATGGCCCTGTCCT

TTTACCAGACAACCATTACCTGTCGACACAAACTGTCCTTTCGAAAGATC

CCAACGAAAAG 3'
``` wherein the sequence of the T7 promoter is underlined, the RBS is underlined and in bold and the first codon is underlined, in bold and in italics.

D. Small Protein B, SmpB

The first element of the system of the invention which is specific for the bacterial species of which it is desired to test the trans-translational activity is the SmpB protein of said bacterial species, or a biologically active fragment of this protein, or else a DNA sequence encoding this protein or this fragment.

Bacterial species. The species of bacterium of which the trans-translational activity can be studied by means of a system of the invention can be any bacterial species or strain. In particular, the bacterium may be a Gram-positive (Gram+) bacterium or a Gram-negative (Gram−) bacterium. A "Gram+ bacterium" is a bacterium which has single-membrane structure and which appears purple using the Gram-staining technique. The Gram+ bacteria include, without limitation, the bacteria belonging to the genera *Staphylococcus, Micrococcus, Lactococcus, Lactobacillus, Clostridium, Bacillus, Streptococcus, Corynebacterium, Enterococcus,* and *Listeria*. A "Gram− bacterium" is a bacterium which, save for some exceptions, has a double-membrane structure which appears pink using the Gram-staining technique. The Gram− bacteria include, without limitation, the bacteria belonging to the genera *Bordetella, Salmonella, Enterobacter, Klebsiella, Acinetobacter, Shigella, Yersinia, Escherichia coli, Vibrio, Pseudomonas, Neisseria, Haemophilus,* and *Agrobacterium*. Alternatively, the bacterium may be a mycobacterium, for example belonging to the *Mycobacterium* genus.

SmpB. As already indicated, the principal process for rescuing blocked bacterial ribosomes is trans-translation, which is carried out by the tmRNA, associated with a basic small protein, SmpB (Small protein B). SmpB is also known as "SsrA-binding protein" and "tmRNA-binding trans-translation protein". The spmB gene, which encodes the SmpB protein, has been identified in all known bacterial species (Karzai et al., Nature Struct. Biol., 2000, 7(6): 449-455). The nucleotide and polypeptide sequences of SmpB have been determined for a considerable number of bacterial species and strains and are available in the databases (GenBank, EMBL Nucleotide Sequence Database, Swiss-Prot, UniProt, tmRNA website, tmRDB, etc.). Those skilled in the art can easily find the sequence(s) which interest(s) them.

The term "the SmpB protein of the bacterial species", as used herein, denotes a molecule consisting of, or essentially consisting of, the polypeptide sequence of the SmpB protein of the bacterial species of which it is desired to test the trans-translation. Preferably, the SmpB protein is isolated or purified. The term "isolated or purified", as used herein for describing a polypeptide or a polynucleotide, denotes a polypeptide or polynucleotide which, by virtue of its origin or its manipulation, is separated from at least some components with which it is naturally associated. Alternatively or additionally, the term "isolated or purified" is intended to mean a polypeptide or polynucleotide which is produced or synthesized by human beings. The SmpB protein of a system according to the invention can be in the form of a fusion protein, in which the polypeptide sequence of SmpB is fused to a given fusion partner sequence. The term "fusion partner sequence" is intended to mean herein a peptide sequence which confers on the fusion protein one or more desirable properties. Thus, a fusion partner sequence can consist of a protein which promotes the expression of SmpB in the host cell during the preparation of the fusion protein, and/or of a protein which facilitates the purification of the fusion protein (for example a Histidine tag), and/or of a protein which increases the stability of the fusion protein (by comparison with non-fused SmpB).

The term "biologically active fragment of the SmpB protein", as used herein, denotes a fragment of the SmpB protein which has approximately the same biological properties as the native SmpB protein, in particular which has the ability to effectively participate in the trans-translation process, in combination with the tmRNA.

In certain embodiments, in particular in the embodiments wherein the two components specific for the bacterial species which are contained in the system of the invention are included in a plasmid/vector; the SmpB protein can be provided in the form of a DNA coding sequence or of a sequence encoding a biologically active fragment of the SmpB protein.

In the case where the bacterial species is *Escherichia coli*, the sequence (EG11782, NC_000913.3:2754896-2755378, *E. coli* K12 substr MG1655) encoding the SmpB protein (483 bp) can be the following sequence SEQ ID NO: 2:

```
ATGACGAAGAAAAAGCACATAAACCTGGTTCAGCGACCATCGCGCTTAA

CAAGCGCGCCCGTCACGAATACTTTATCGAAGAAGAGTTCGAAGCGGGAC

TTGCCCTGCAAGGCTGGGAAGTTAAATCCCTGCGCGCAGGAAAAGCCAAT

ATCAGCGACAGCTACGTCCTTCTGCGTGACGGAGAGGCATTTCTGTTTGG
```

-continued

CGCTAACATCACGCCAATGGCCGTGGCCTCCACGCATGTGGTGTGCGATC

CTACCCGTACCCGCAAGTTACTTCTCAACCAGCGCGAACTGGACTCATTG

TACGGTCGCGTCAATCGAGAAGGCTATACCGTAGTGGCGCTCTCCCTGTA

CTGGAAAAATGCCTGGTGCAAAGTGAAAATCGGCGTCGCCAAAGGTAAGA

AACAGCACGATAAACGTTCAGATATCAAAGAGCGCGAATGGCAGGTGGAT

AAAGCACGTATCATGAAAAACGCCCACCGTTAA.

In the case where the bacterial species is *Enterococcus faecium*, the sequence (NC_017960.1:c2002719-2002255 *Enterococcus faecium* DO chromosome) encoding the SmpB protein can be the following sequence SEQ ID NO: 3:

ATGCCAAAAGGCGAGGGAAAATTAATTGCACAAAACAAGAAAGCTCGCCA

TGATTATTCGATCATCGACACGATGGAAGCAGGGATGGTCTTGCAAGGAA

CCGAGATCAAGTCGATACGAAACAGCCGGATCAATCTAAAAGATGGATTT

ATTCGCGTCCGCAACGGAGAAGCTTTCTTGCATAATGTTCATATCAGTCC

TTATGAACAAGGAAATATTTTTAATCATGATCCGTTGCGCACGAGAAAGT

TATTATTACACAAAAAACAAATCATCCGGCTTGAAAATGAATTGAAAAAT

ACTGGAATCACTGTTGTTCCTTTAAAAGTCTATATTCGTAACGGCTATGC

CAAGGTATTGATTGGTCTGGCGAAAGGGAAAAAATCTTATGATAAACGGG

AAGATTTGAAACGAAAAGATATCGATCGACAAATTGATCGAACATTAAAA

AATTTCTCTAGATAA.

In the case where the bacterial species is *Staphylococcus aureus*, the sequence (NZ_GG774480 *Staphylococcus aureus* subsp. *aureus* ATCC 51811) encoding the SmpB protein can be the following sequence SEQ ID NO: 4:

ATGGCTAAGAAGAAATCACCAGGTACATTAGCGGAAAATCGTAAAGCAAG

ACATGATTATAATATTGAAGACACGATTGAAGCGGGAATCGTATTACAAG

GTACAGAAATAAAATCGATTCGCCGAGGTAGTGCTAACCTTAAAGATAGT

TACGCGCAAGTTAAAAACGGTGAAATGTATTTGAATAATATGCATATAGC

ACCATACGAAGAAGGGAATCGTTTTAATCACGATCCTCTTCGTTCTCGAA

AATTATTATTGCATAAACGTGAAATCATTAAATTGGGTGATCAAACACGT

GAAATTGGTTATTCGATTGTGCCATTAAAGCTTTATTTGAAGCATGGGCA

TTGTAAAGTATTACTTGGTGTCGCACGAGGTAAGAAAAAATATGATAAAC

GTCAAGCTTTGAAAGAAAAGCAGTCAAACGAGATGTTGCGCGCGATATG

AAAGCCCGTTATTAA.

In the case where the bacterial species is *Klebsiella pneumoniae*, the sequence (NC_017540.1:3742807-3743289 *Klebsiella pneumoniae* KCTC 2242) encoding the SmpB protein can be the following sequence SEQ ID NO: 5:

ATGACTAAGAAAAAAGCCCACAAACCTGGATCAGCCACCATTGCGCTGAA

TAAACGCGCCCGTCACGAATACTTTATCGAAGATGAATACGAGGCTGGTC

TCGCCCTGCAGGGCTGGGAAGTCAAATCCCTGCGTGCAGGCAAAGCCAAC

ATCGGCGATAGCTATGTCATCCTGAAGGATGGCGAAGCCTTCCTGTTCGG

CGCCAACTTTACGCCCATGGCCGTGGCTTCCACCCACTATGTCTGCGACC

CGACGCGCACCCGTAAGCTGCTGCTCAACCAGCGTGAGCTGGACACGCTG

TACGGCCGCATTAACCGCGAAGGTTACACCGTCGTCGCCCTGTCGCTGTA

CTGGAAGAACGCCTGGTGCAAAGTGAAAATCGGCGTCGCCAAAGGTAAGA

AACAGCACGACAAGCGTACCGACCTGAAAGATCGTGAATGGGCGCTGGAC

AAGGCGCGTATTATGAAGCACGCCGGACGTTAA

In the case where the bacterial species is *Acinetobacter baumannii*, the sequence (NZ_KB849843.1, *Acinetobacter baumannii* NIPH 201 acLrm-supercont1.3) encoding the SmpB protein can be the following sequence SEQ ID NO: 6:

ATGGCGAAAGCAACAGTAGTAAAGAAACATAATGGCGGAACCATCGCACA

AAACAAACGTGCCCGTCATGATTATTTTATCGAAGAAAAATTTGAAGCTG

GCATGTCTTTACTAGGCTGGGAAGTAAAATCTTTACGTGCCGGTCGTATG

AGTTTGACAGAAAGTTATGTCATTTTTAAAAATGGTGAAGCATTCTTATT

TGGTGCTCAGATTCAACCACTCCTTTCTGCATCTACACATATTGTGCCGG

AAGCTACACGTACACGAAAATTATTATTATCTCGTCGTGAACTTGAAAAG

CTTATGGGTGCGGTGAACCAAAAAGGTTATTCGTGCGTTCCATTAGCATG

TTACTGGAAAGGTCATCTGGTTAAGCTTGAAATTGCACTCGTGAAAGGTA

AACAACTTCACGATAAACGAGCGACTGAAAAAGAACGTGACTGGCAACGT

GATAAAGCACGTATATTTCATAAGTAA.

In the case where the bacterial species is *Pseudomonas aeruginosa*, the sequence (NC_002516.2:5353783-5354262 *Pseudomonas aeruginosa* PAO1 chromosome) encoding the SmpB protein can be the following sequence SEQ ID NO: 7:

ATGGCTAAGCAGAAGAAACACCCTTCGGGGACCATCGCGCAGAACAAGAA

GGCTCTGCACGACTATTTCATCGAACAACGCTTCGAGGCGGGCGTCGCCC

TGGCGGGCTGGGAAGTGAAAAGCCTGCGCGCCGGCAAGGCCCAGTTGGTC

GACAGCTACGTGCTGCTCAAGGATGGCGAGGCCTGGCTGCTCGGCAGCCA

CATCACGCCCCTGACCACCGCCAGCACGCACGTGATCGCCGACCCGGTGC

GCACGCGCAAGCTGCTGCTGCACAAGCGCGAACTGGGCAAGCTGTTCGGC

GCCGTGCAACAGAAGGGCTACGCCTGCGTCGCTCTGTCGATGTACTGGAA

GAAGCACCTGGTCAAGTGCGAGATCGCCCTGGCCAAGGGCAAGAAGGACT

TCGACAAGCGCCACACCGAGAAGGAGCGCGACTCCGATCGGGAGATCCAG

CGCGCCATGCGCCACGGCAAGGACGACTGA.

In the case where the bacterial species is *Enterobacter cloacae*, the sequence (NC_016514.1, *Enterobacter cloacae* EcWSU1) encoding the SmpB protein can be the following sequence SEQ ID NO: 8:

```
ATGACGAAGAAAAAAGCACATAAACCAGGCTCGGCGACCATTGCGCTCAA

CAAGCGTGCTCGCCACGAGTATTTTATTGAAGAAGAATTCGAAGCTGGCC

TTGCATTGCAGGGCTGGGAAGTAAAATCGCTGCGCGCCGGGAAAGCCAAT

ATCGGTGATAGTTACGTGATCCTGAAAGATGGCGAAGCCTTCCTGTTCGG

TGCCAACTTCACGCCGCTGACCGTCGCCTCGTCACACTACGTGTGTGACC

CAACGCGTACCCGTAAGCTGCTGTTGAACAAGCGCGAACTGGAGTCCCTT

TATGGGCGCATTAACCGTGAAGGCTTCACCGTGGTTGCCCTGTCGCTGTA

CTGGAAAAATGCCTGGTGCAAAGTGAAAGTTGGCGTCGCGAAGGGTAAAA

AACAGCACGACAAACGTACCGATCTGAAAGAGCGCGAATGGCAGCTCGAC

AAAGCACGTATTATGAAAAACGCAGGACGTTGA.
```

In the case where the bacterial species is *Mycobacterium tuberculosis*, the sequence (NC_016934.1 *Mycobacterium tuberculosis* UT205) encoding the SmpB protein can be the following sequence SEQ ID NO: 9:

```
GTGTCCAAGTCGTCGCGTGGCGGCCGGCAGATCGTTGCCAGCAATCGCAA

AGCCCGGCACAACTATTCGATCATCGAGGTGTTCGAGGCCGGGGTTGCGC

TGCAAGGCACGGAGGTGAAGAGCCTGCGGGAAGGGCAGGCGTCGCTGGCC

GATTCGTTCGCCACCATCGACGACGGCGAAGTGTGGCTGCGCAACGCGCA

CATCCCGGAATACCGGCACGGCAGCTGGACCAACCACGAGCCGCGACGCA

ACCGCAAACTGCTGTTGCATCGCCGCCAGATCGACACCTTGGTCGGCAAG

ATCCGCGAAGGCAACTTCGCCCTGGTGCCGTTGTCGCTGTATTTCGCCGA

AGGCAAGGTCAAGGTTGAGCTTGCGCTGGCCCGAGGCAAGCAAGCCCGCG

ACAAACGCCAGGACATGGCCCGTCGTGATGCCCAGCGTGAAGTGCTCCGC

GAGTTGGGTCGGCGCGCTAAGGGCATGACCTGA.
```

As those skilled in the art will recognize, all the variants of the sequences SEQ ID Nos 2-9 which encode the SmpB protein of the bacterial species of interest can also be used.

Preparation of the SmpB polynucleotide and polypeptide sequences. The polynucleotide or polypeptide sequences of the SmpB protein can be prepared by any appropriate method. As indicated above, the techniques for isolating or cloning a gene or a nucleotide sequence encoding a protein or a domain specific for a protein are known in the art. The methods for preparing a known polypeptide sequence include chemical methods (R. B. Merrifield, J. Am. Chem. Soc. 1963, 85: 2149-2154; "*Solid Phase Peptide Synthesis*", Methods in Enzymology, G. B. Fields (Ed.), 1997, Academic Press: San Diego, Calif.), and recombinant methods (Sambrook et al., *Molecular Cloning: A Laboratory Manual*, 2$^{nd}$ Ed., 1989, Cold Spring Harbor Press: Cold Spring, N.Y.) using host cells.

The examples reported at the end of the present document describe a recombinant method for preparing an SmpB protein labeled with a Histidine tag, in the case of *Escherichia coli*. In this method, the sequence encoding the SmpB protein was cloned into the pET22b+ vector between the NdeI and XhoI restriction sites so as to add thereto a histidine tag (6His) for purification on an affinity column.

E. Modified tmRNA

The second element of the system of the invention, which is specific for the bacterial species of which it is desired to test the trans-translational activity, is the transfer-messenger RNA (tmRNA) of said bacterial species, modified such that the portion of sequence encoding the proteolysis tag is replaced with a sequence encoding the 11$^{th}$ domain of GFP. In certain embodiments, the system of the invention comprises the modified tmRNA in the form of a DNA sequence of which the transcription produces the modified tmRNA.

tmRNA. The tmRNA is also known under the name 10Sa RNA and under its genetic name SsrA. At the current time, the SsrA gene which encodes the tmRNA has been found in all bacterial genomes sequenced. The tmRNA is a structured RNA, a few hundred nucleotides long (363 in *Escherichia coli*). It bears a domain structurally similar to transfer RNAs ("tRNA-like domain" or TLD) which can be aminoacylated by AlaRS, and an internal coding sequence ("mRNA-like domain" or MLD) which has a stop codon and encodes a proteolysis tag.

The tmRNA sequences and the DNA sequences encoding these tmRNAs have been determined for a considerable number of bacterial species and strains and are available in the databases (GenBank, EMBL Nucleotide Sequence Database, Swiss-Prot, UniProt, tmRNA website, tmRDB, etc.). Those skilled in the art can easily find the sequence(s) which interest(s) them.

For example, in certain embodiments, the DNA sequence encoding the tmRNA of the bacterial species (wherein the sequence of the MLD which encodes the proteolysis tag is represented in bold and underlined, and wherein the pairing sequence forming the H5 helix (see below) is in italics and in bold), is:

in the case of *Escherichia coli*:

```
                                       (SEQ ID NO: 10)
GGGGCTGATTCTGGATTCGACGGGATTTGCGAAACCCAAGGTGCATGCCG

AGGGGCGGTTGGCCTCGTAAAAAGCCGCAAAAAATAGTCGCAAACGACGA

AAACTACGCTTTAGCAGCTTAATAACCTGCTTAGAGCCCTCTCTCCCTAG

CCTCCGCTCTTAGGACGGGATCAAGAGAGGTCAAACCCAAAAGAGATCG

CGTGGAAGCCCTGCCTGGGGTTGAAGCGTTAAAACTTAATCAGGCTAGTT

TGTTAGTGGCGTGTCCGTCCGCAGCTGGCAAGCGAATGTAAAGACTGACT

AAGCATGTAGTACCGAGGATGTAGGAATTTCGGACGCGGGTTCAACTCCC

GCCAGCTCCACCA;
``` in the case of *Enterococcus faecium* (10031 *Enterococcus faecium* CRL1879):

```
                                       (SEQ ID NO: 11)
GGGGACGTTACGGATTCGACAGGCACAGTCGAGCTTGAATTGCGTTTCGT

AGGTTACGTCTACGTAAAAACGTTACAGTTAAATATAACTGCTAAAAACG

AAAACAACTCTTACGCTTTAGCTGCCTAAAAACAGTTAGCGTAGATCCTC

TCGGCATCGCCCATGTGCTCGAGTAAGGGTCCTAACTTTAGTGGGATACG

TTTCAACTTTCCGTCTGTAAGTTGAAAAAGAGAACATCAGACTAGCGATA

CAGAATGCCTGTCACTCGGCAAGCTGTAAAGTGAATCCTTAAATGAGTTG

ACTATGAACGTAGATTTTTAAGTGGCGATGTGTTTGGACGCGGGTTCGAC

TCCCGCCGTCTCCATTG;
``` in the case of *Staphylococcus aureus* (10371 *Staphylococcus aureus* subsp. *aureus* ATCC 51811):

(SEQ ID NO: 12)
GGGGACGTTCATGGATTCGACAGGGGTCCCCCGAGCTCATTAAGCGTGTC

GGAGGGTTGTCTTCGTCATCAACACACACAGTTTATAATAACTGGCAAAT

CAAACAATAATTTCGCAGTAGCTGCCTAATCGCACTCTGCATCGCCTAAC

AGCATTTCCTATATGCTGTTAACGCGATTCAACCTTAATAGGATATGCTA

AACACTGCCGTTTGAAGTCTGTTTAGAAGAAACTTAATCAAGCTAGCATC

ATGTTGGTTGTTTATCACTTTTCATGATGCGAAACCTTTCGATAAACTAC

ACACGTAGAAAGATGTGTATCAGGACCTCTGGACGCGGGTTCAAATCCCG

CCGTCTCCATAT;

in the case of *Klebsiella pneumoniae* (12816 *Klebsiella pneumoniae* KCTC 2242):

(SEQ ID NO: 13)
GGGGCTGATTCTGGATTCGACGGGATTTGCGAAACCCAAGGTGCATGCCG

AGGGGCGGTTGGCCTCGTAAAAAGCCGCAAAAAATAGTCGCAAACGACGA

AAACTACGCTTTAGCAGCTTAATAACCTGCTCTGAGCCCTCTCTCCCTAG

CTTCCGCTCTTAAGACGGGATCAAAGAGAGGTCAAACCCAAAAGAGATC

GCGTGGATGCCCTGCCTGGGGTTGAAGCGTTAAATCTCATCAGGCTAGTT

TGTTAGTGGCGTGTCTGTCCGCAGCTGGCAAGCGAATGTAAAGACTGACT

AAGCATGTAGTGCCGAGGATGTAGGAATTTCGGACGCGGGTTCAACTCCC

GCCAGCTCCACCA;

in the case of *Acinetobacter baumannii* (10722 *Acinetobacter baumannii* NIPH 201):

(SEQ ID NO: 14)
GGGGATGTTATTGGCTTCGACGCCGGTGATGAAACTCATAGATGCATGCC

GAGAGCGCATTTTCTCTCGTAAATAAAATTTGCATTTAAATAGTCGCAAA

CGACGAAACTTACGCTCTAGCTGCCTAAGGGCCGCTTGTCCGCTTCCTAG

AATACTTGTGGTCTGGGAACCCGACTGAAGCGCACGCACACAAGTCCGTA

TAGAGTCAAGCCTCGGGGCTTTATACCAAACTTAGAGGATCGCACTTTGT

ACCCTGTTCGTCGGGTCACTTGGTGTTAAAACAATAGACGATATCTAAGC

ATGTAGTATTCTCGAGCGTAGTGCTGGCGGACGCGGGTTCAACTCCCGCC

ATCTCCACCA;

in the case of *Pseudomonas aeruginosa* (NC_002516.2: c901872-901520 *Pseudomonas aeruginosa* PAO1 chromosome, complete genome):

(SEQ ID NO: 15)
GGGGCCGATTAGGATTCGACGCCGGTAACAAAACTTGAGGGGCATGCCGA

GCTGGTAGCAGAACTCGTAAATTCGCTGCTGCAAACTTATAGTTGCCAAC

GACGACAACTACGCTCTAGCTGCTTAATGCGGCTAGCAGTCGCTAGGGGA

TGCCTGTAAACCCGAAACGACTGTCAGATAGAACAGGATCGCCGCCAAGT

TCGCTGTAGACGTAACGGCTAAAACTCATACAGCTCGCTCCAAGCACCCT

GCCACTCGGGCGGCGCGGAGTTAACTCAGTAGAGCTGGCTAAGCATGTAG

AACCGATAGCGGAGAGCTGGCGGACGGGGGTTCAAATCCCCCCGGCTCCA

CCA;

in the case of *Enterobacter cloacae* (11123 *Enterobacter cloacae* EcWSU1):

(SEQ ID NO: 16)
GGGGCTGATTCTGGATTCGACGGGATTTGCGAAACCCAAGGTGCATGCCG

AGGGGCGGTTTGCCTCGTAAAAAGCCGCAAAAAAATAGTCGCAAACGACG

AAAACTACGCTTTAGCAGCTTAATAACCTGCTCTGAGCCCTCTCTCCCTA

GCTTCCGCTCTTAAGACGGGGATTCAAGAGAGGTCAAACCCAAAAGAGAT

CGCGTGGAAGCCCTGCCTGGGGTTGAAGCGTTAAAACTAATCAGGCTAGT

ACGTTAGTGGCGTGTTTGTTCGCAGCTGGCGTGCGAATGTAAAGACAAAC

TAAGCATGTAGTACCGAGGATGTAGAAATTTCGGACGCGGGTTCAACTCC

CGCCAGCTCCACCA;
and in the case of *Mycobacterium tuberculosis* (10001 *Mycobacterium tuberculosis* UT205):

(SEQ ID NO: 17)
GGGGCTGAACGGTTTCGACTTCGCGCATCGAATCAAGGGAAGCGTGCCGG

TGCAGGCAAGAGACCACCGTAAGCGTCGTTGCGACCAAATAAGCGCCGAT

TCACATCAGCGCGACTACGCTCTCGCTGCCTAAGCGACGGCTAGTCTGTC

AGACCGGGAACGCCCTCGGCCCGGACCCTGGCATCAGCTAGAGGGATCCA

CCGATGAGTCCGGTCGCGGGACTCCTCGGGACAACCACAGCGACTGGGAT

CGTCATCTCGGCTAGTTCGCGTGACCGGGAGATCCGAGCAGAGGCATAGC

GAACTGCGCACGGAGAAGCCTTGAGGGAATGCCGTAGGACCCGGGTTCGA

TTCCCGGCAGCTCCACCG.

Modified tmRNA. The tmRNA of the reporter system for trans-transcription according to the invention is a modified tmRNA, and more specifically the tmRNA of the bacterial species of which the portion of sequence encoding the proteolysis tag is replaced with a sequence encoding the 11$^{th}$ domain of GFP.

As already indicated above, the term "11$^{th}$ domain of GFP" denotes the β-domain which is in the C-terminal portion of GFP. In certain preferred embodiments of the invention, the 11$^{th}$ domain of GFP, or of GFP11, is the 11$^{th}$ domain of Superfolder GFP, which is a short peptide of 16 amino acids (Cabantous & Waldo, Nature Methods, 2006, 3(10): 845-854; Kamiyama et al., Nature Commun., 2016, 7: 11046). Preferably, in the translation product, the sequence of the proteolysis tag is replaced with the following sequence:

(SEQ ID NO: 18)
ARDHMVLHEYVNAAGIT, which contains the conserved first alanine of the native tmRNA plus the sequence of 16 amino acids of the 11$^{th}$ domain of GFP, and which is encoded by the following DNA:

(SEQ ID NO: 19)
GCACGTGACCACATGGTCCTTCATGAGTACGTAAATGCTGCTGGGATTAC

ATAA.

The term "proteolysis tag" or "peptide tag degraded by trans-translation-specific proteases" is intended to mean the sequence of the peptide tag added, by the tmRNA, to the incomplete protein blocked in the ribosome, during the trans-translation process in the species of bacterium of which it is desired to test the trans-translation. This tag is also called "SsrA tag", "SsrA-tail", "queue SsrA" or "degradation SsrA tag", from the name of the SsrA gene which encodes the tmRNA in the bacteria, or else "peptide sequence encoded by the tmRNA".

The sequences of the proteolysis tags are known in the art for a large number of bacterial species and strains (see, for example, the list provided on the websites: www.ag.auburn-.edu/mirror/tmRDB/peptide/peptidephylolist.html and http://bioinformatics.sandia.gov/tmrna/).

As shown in FIG. 2, in the tmRNA molecule, a portion of the sequence of the MLD domain (domain which encodes the proteolysis tag) pairs with the sequence of a downstream (3') region, thus forming a helix, called "H5 helix". The H5 helix is a structure which is conserved within the tmRNAs of various bacterial species. Thus, preferably, with the aim of conserving the presence of an H5 helix in the modified tmRNA according to the invention, the sequence 3' of the sequence encoding the proteolysis tag is replaced with a sequence which pairs with a region of the sequence encoding the 11$^{th}$ domain of GFP so as to form an H5 helix.

Thus, preferably, the modified tmRNA of the reporter system for trans-translation according to the invention is the tmRNA of the bacterial species of interest, modified such that:
  (1) the portion of sequence encoding the proteolysis tag is replaced with a sequence encoding the 11$^{th}$ domain of GFP, and
  (2) the sequence 3' of said portion of sequence is replaced with a sequence which partially pairs with the sequence encoding the 11$^{th}$ domain of GFP so as to form a helix.

The expression "sequence which partially pairs with the sequence encoding the 11$^{th}$ domain of GFP", is intended to mean herein a sequence which pairs only with a specific region (or portion) of the sequence encoding the 11$^{th}$ domain of GFP in order to form a helix (and not with all of the sequence encoding the 11$^{th}$ domain of GFP).

In the embodiments wherein the DNA sequence which encodes the 11$^{th}$ domain of GFP is the sequence:

(SEQ ID NO: 19)
GCACGTGACCACATGGTCCTTCATGAGTACGTAAATGCTGCTGGGATTAC

ATAA, the sequence which partially pairs with this DNA sequence so as to form a helix can be the following sequence:

(SEQ ID NO: 20)
TAACCTAATCCTAGC

Thus, in certain particular embodiments of the present invention, the DNA sequence encoding the modified tmRNA according to the invention is the following, wherein the sequence encoding the 11$^{th}$ domain of GFP (SEQ ID NO: 19) is represented in bold and underlined, and wherein the sequence which partially pairs with the sequence encoding the 11$^{th}$ domain of GFP so as to form a helix (SEQ ID NO: 20) is in italics and bold:

in the case of *Escherichia coli*:

(SEQ ID NO: 21)
GGGGCTGATTCTGGATTCGACGGGATTTGCGAAACCCAAGGTGCATGCCG

AGGGGCGGTTGGCCTCGTAAAAAGCCGCAAAAAATAGTCGCACGTGACCA

CATGGTCCTTCATGAGTACGTAAATGCTGCTGGGATTACATAA*TAACCTA*

*ATCCTAGCCCTCTCTCCCTAGCCTCCGCTCTTAGGACGGGGATCAAGAGA*

GGTCAAACCCAAAAGAGATCGCGTGGAAGCCCTGCCTGGGGTTGAAGCGT

TAAAACTTAATCAGGCTAGTTTGTTAGTGGCGTGTCCGTCCGCAGCTGGC

AAGCGAATGTAAAGACTGACTAAGCATGTAGTACCGAGGATGTAGGAATT

TCGGACGCGGTTCAACTCCCGCCAGCTCCACCA;

in the case of *Enterococcus faecium*:

(SEQ ID NO: 22)
GGGGACGTTACGGATTCGACAGGCACAGTCGAGCTTGAATTGCGTTTCGT

AGGTTACGTCTACGTAAAAACGTTACAGTTAAATATAACTGCACGTGACC

ACATGGTCCTTCATGAGTACGTAAATGCTGCTGGGATTACATAA*TAACCT*

*AATCCTAGCGATCCTCTCGGCATCGCCCATGTGCTCGAGTAAGGGTCCTA*

ACTTTAGTGGGATACGTTTCAACTTTCCGTCTGTAAGTTGAAAAAGAGAA

CATCAGACTAGCGATACAGAATGCCTGTCACTCGGCAAGCTGTAAAGTGA

ATCCTTAAATGAGTTGACTATGAACGTAGATTTTTAAGTGGCGATGTGTT

TGGACGCGGGTTCGACTCCCGCCGTCTCCATTG;

in the case of *Staphylococcus aureus*:

(SEQ ID NO: 23)
GGGGACGTTCATGGATTCGACAGGGGTCCCCCGAGCTCATTAAGCGTGTC

GGAGGGTTGTCTTCGTCATCAACACACACAGTTTATAATAACTGCACGTG

ACCACATGGTCCTTCATGAGTACGTAAATGCTGCTGGGATTACATAA*TAA*

*CCTAATCCTAGCATCGCCTAACAGCATTTCCTATATGCTGTTAACGCGAT*

TCAACCTTAATAGGATATGCTAAACACTGCCGTTTGAAGTCTGTTTAGAA

GAAACTTAATCAAGCTAGCATCATGTTGGTTGTTTATCACTTTTCATGAT

GCGAAACCTTTCGATAAACTACACACGTAGAAAGATGTGTATCAGGACCT

CTGGACGCGGGTTCAAATCCCGCCGTCTCCATAT;

in the case of *Klebsiella pneumoniae*:

(SEQ ID NO: 24)
GGGGCTGATTCTGGATTCGACGGGATTTGCGAAACCCAAGGTGCATGCCG

AGGGGCGGTTGGCCTCGTAAAAAGCCGCAAAAAATAGTCGCACGTGACCA

CATGGTCCTTCATGAGTACGTAAATGCTGCTGGGATTACATAA*TAACCTA*

*ATCCTAGCCCTCTCTCCCTAGCTTCCGCTCTTAAGACGGGGATCAAAGAG*

AGGTCAAACCCAAAAGAGATCGCGTGGATGCCCTGCCTGGGGTTGAAGCG

TTAAATCTCATCAGGCTAGTTTGTTAGTGGCGTGTCTGTCCGCAGCTGGC

-continued
AAGCGAATGTAAAGACTGACTAAGCATGTAGTGCCGAGGATGTAGGAATT

TCGGACGCGGGTTCAACTCCCGCCAGCTCCACCA;

in the case of *Acinetobacter baumannii*:

(SEQ ID NO: 25)
GGGGATGTTATTGGCTTCGACGCCGGTGATGAAACTCATAGATGCATGCC

GAGAGCGCATTTTCTCTCGTAAATAAAATTTGCATTTAAATAGTCGCACG

TGACCACATGGTCCTTCATGAGTACGTAAATGCTGCTGGGATTACATAAT

A*ACC*TAA*TCC*TAGCGTCCGCTTCCTAGAATACTTGTGGTCTGGGAACCCG

ACTGAAGCGCACGCACACAAGTCCGTATAGAGTCAAGCCTCGGGGCTTTA

TACCAAACTTAGAGGATCGCACTTTGTACCCTGTTCGTCGGGTCACTTGG

TGTTAAAACAATAGACGATATCTAAGCATGTAGTATTCTCGAGCGTAGTG

CTGGCGGACGCGGGTTCAACTCCCGCCATCTCCACCA;

in the case of *Pseudomonas aeruginosa*:

(SEQ ID NO: 26)
GGGGCCGATTAGGATTCGACGCCGGTAACAAAACTTGAGGGGCATGCCGA

GCTGGTAGCAGAACTCGTAAATTCGCTGCTGCAAACTTATAGTTGCACGT

GACCACATGGTCCTTCATGAGTACGTAAATGCTGCTGGGATTACATAATA

A*CC*TAA*TCC*TAGCCAGTCGCTAGGGGATGCCTGTAAACCCGAAACGACTG

TCAGATAGAACAGGATCGCCGCCAAGTTCGCTGTAGACGTAACGGCTAAA

ACTCATACAGCTCGCTCCAAGCACCCTGCCACTCGGGCGGCGCGGAGTTA

ACTCAGTAGAGCTGGCTAAGCATGTAGAACCGATAGCGGAGAGCTGGCGG

ACGGGGTTCAAATCCCCCGGCTCCACCA;

in the case of *Enterobacter cloacae*:

(SEQ ID NO: 27)
GGGGCTGATTCTGGATTCGACGGGATTTGCGAAACCCAAGGTGCATGCCG

AGGGGCGGTTTGCCTCGTAAAAAGCCGCAAAAAAATAGTCGCACGTGACC

ACATGGTCCTTCATGAGTACGTAAATGCTGCTGGGATTACATAATAACCT

AA*TCC*TAGCCC*TC*TCCCTAGCTTCCGCTCTTAAGACGGGGATTCAAGA

GAGGTCAAACCCAAAAGAGATCGCGTGGAAGCCCTGCCTGGGGTTGAAGC

GTTAAAACTAATCAGGCTAGTACGTTAGTGGCGTGTTTGTTCGCAGCTGG

CGTGCGAATGTAAAGACAAACTAAGCATGTAGTACCGAGGATGTAGAAAT

TTCGGACGCGGGTTCAACTCCCGCCAGCTCCACCA;
and in the case of *Mycobacterium tuberculosis*:

(SEQ ID NO: 28)
GGGGCTGAACGGTTTCGACTTCGCGCATCGAATCAAGG-
GAAGCGTGCCGGTG

CAGGCAAGAGACCACCGTAAGCGTCGTTGCGACCAAATAAGCGCACGTGA

CCACATGGTCCTTCATGAGTACGTAAATGCTGCTGGGATTACATAATAAC

C*TAATCC*TAGCTGTCAGACCGGGAACGCCCTCGGCCCGGACCCTGGCATC

AGCTAGAGGGATCCACCGATGAGTCCGGTCGCGGGACTCCTCGGGACAAC

-continued
CACAGCGACTGGGATCGTCATCTCGGCTAGTTCGCGTGACCGGGAGATCC

GAGCAGAGGCATAGCGAACTGCGCACGGAGAAGCCTTGAGGGAATGCCGT

AGGACCCGGGTTCGATTCCCGGCAGCTCCACCG.

Preparation of a modified tmRNA according to the invention. The polynucleotide sequences can be prepared by any appropriate method. As already indicated above, the techniques for isolating or cloning a gene or a nucleotide sequence encoding a protein or a specific domain of a protein are known in the art. The examples presented at the end of this document describe a method for preparing plasmids comprising a DNA sequence of which the transcription produces a modified *E. coli* tmRNA and the production of the modified tmRNA in vivo (i.e. in a bacterial cell medium, and more specifically in an *E. coli* strain) and the production of the modified tmRNA in vitro (that is to say in cell-free medium).

F. Vectors or Plasmids

In certain embodiments, at least one of the three components of a reporter system according to the invention is inserted into an appropriate vector or plasmid or produced in vitro by PCR. In other embodiments, the three components of a system according to the invention are inserted into an appropriate vector or plasmid. For example, the sequence encoding the first 10 domains of GFP and not comprising a stop codon can be inserted into a first plasmid (or vector), and the sequence encoding SmpB and the sequence encoding the modified tmRNA can be inserted into a second plasmid (or vector). Alternatively, the three components of a system according to the invention can be inserted into one and the same plasmid (or vector).

Numerous vectors and plasmids can be used in the context of the present invention. However, as known by those skilled in the art, the vector or plasmid must either be suitable for the use in the species or the strain of bacterium in which the reporter system is intended to be used, or be a broad-spectrum vector or plasmid, for example a broad-spectrum vector suitable for use in Gram-bacteria or a broad-spectrum vector suitable for use in Gram+ bacteria.

The term "vector", is intended to mean herein a DNA molecule which is without implied distinction in single-stranded or double-stranded form. A recombinant vector according to the invention is preferably a plasmid vector. Thus, in certain embodiments of the invention, the vector is a plasmid. The term "plasmid" is intended to mean herein a double-stranded circular DNA molecule.

A vector/plasmid generally comprises all the appropriate sequences required for the transcription/translation of the coding sequence that it contains (initiation sequences, transcription stop sequences, selectable markers, etc.). A vector/plasmid that is of use in the context of the invention may be a vector which enables inducible expression of the coding sequence, that is to say which enables the specific induction of the expression in response to the presence of a particular compound, known as inducer. Thus, preferably, a vector/plasmid that is of use in the context of the invention contains a strong promoter (if deleted from the cassette), which is readily inducible and the activity of which is negligible in the absence of specific inducers. It generally carries the regulator gene which makes it possible to control the expression of the cassette. Examples of inducers which are suitable for use in the bacteria include, without limitation, arabinose which is used with the araC regulator and IPTG (isopropyl β-D-1-thiogalactopyranoside) which is used with the LacI repressor. A plasmid vector may also comprise restriction sites. The term "restriction site" denotes a particular sequence of nucleotides which is recognized by a restriction enzyme as a cleavage site in the DNA molecule. The restriction sites and their use in molecular biology are known in the art (www.neb.com/tools-and-resources/selection-charts/alphabetized-list-of-recognition-specificities) and those skilled in the art know how to select restriction sites as a function of the desired use. Examples of restriction sites include, without limitation, the restriction sites recognized by the BamHI, HindIII, KpnI, NdeI, ApaI, XbaI, BglII and EcoRI enzymes. Examples of plasmids include pET, pUC, pBAD, pGEMEX, etc.

II—Protein Synthesis System

A reporter system for the trans-translational activity of a bacterial species according to the invention is used in combination with a bacterial system for protein synthesis. This is because, in order to be able to test the trans-translation activity, it is necessary to first of all carry out a translation step (that is to say a protein synthesis step). The protein synthesis system that can be used in communication with a reporter system according to the invention may be an in vivo system (that is to say a bacterial cellular system) or an in vitro system (that is to say a cell-free protein production system).

Those skilled in the art will recognize that it is possible to use a reporter system for the trans-translational activity of a bacterial species with a protein synthesis system of the same bacterial species for a test under homologous conditions. Alternatively, it is possible to use a reporter system for the trans-translational activity of a bacterial species with a protein synthesis system of even another bacterial species for a test under heterologous conditions.

A. Reconstituted Cell-Free Protein Synthesis System

The term "protein production cell-free system" is intended to mean herein a biochemical system enabling the synthesis of a protein in the absence of a cell. Such a system comprises all the elements required for the production of proteins in the absence of a bacterial cell. In particular, this system comprises, inter alia, the transcriptional and translational machinery originating from the bacterial cell. Indeed, the cell-free system makes it possible to convert the information contained in the DNA template by virtue of the coupling of the transcription (mRNA generation) and translation (protein generation) reactions.

Cell-free systems for protein production have been well known to those skilled in the art for several tens of years (for reviews, see for example, Carlson et al., Biotechnol. Adv., 2012, 30(5): 1185-1194; Whittaker, Biotechnol. Lett., 2013, 35(2): 143-152; Tuckey et al., Curr. Protoc. Mol. Biol., 2014, 108:16.31.1-22. doi: 10.1002/0471142727.mb1631s108; Zemella et al., Chembiochem., 2015, 16(17): 2420-2431), and numerous methods available for synthesizing proteins in cell-free systems (see for example "Cell-Free Protein Synthesis: Methods and Protocols", Edited by A. S. Spirin and J. R. Swartz, 2008, Wiley-VCH, Weinheim, Germany). It is also possible to use kits provided by numerous companies, such as, for example, Qiagen, Ambion, Promega, Invitrogen, Thermo Scientific, Roche Diagnostics, CellFree Sciences & Co, etc.

An example of a cell-free protein production system is the reconstituted cell-free protein synthesis system (PURE for Protein Synthesis Using Recombinant Elements). Thus, in certain preferred embodiments, a reporter system for the trans-translational activity of a bacterial species according to the invention is used in combination with a reconstituted cell-free protein synthesis system.

The PURE approach is based on the modular reconstitution of the translational machinery of the cell from affinity-purified protein components (Shimizu et al., Nature Biotechnol., 2001, 19(8): 751-755; Shimizu et al., Methods, 2005, 36(3): 299-304; Shimizu and Ueda, Methods Mol. Biol., 2010, 608: 11-21). Compared with a conventional cell-free protein production system based on the use of cell extracts, a reconstituted cell-free protein synthesis system does not contain cell contaminants, such as proteases and nucleases which inhibit protein synthesis.

The PURE cell-free protein synthesis system has been sold, for example, under the tradenames PURESYSTEM® from Cosmo Bio (Japan) and PUREXPRESS® from New England Biolabs (Beverly, Mass., United States). Thus, in certain particular embodiments, a reporter system for trans-translational activity according to the invention is used in combination with a commercial kit of PURE type.

In other particular embodiments, a reporter system for trans-translational activity according to the invention is used with a cell-free protein synthesis system, the components of which are reassembled by the user. A reconstituted cell-free protein synthesis system constitutes all the elements required for protein production in the absence of a bacterial cell.

In particular, the reconstituted cell-free protein synthesis system comprises the transcription and translational machinery originating from the bacterial cell, namely the ribosome.

Ribosome. Ribosomes are ribonucleoprotein complexes (that is to say compounds of proteins and of RNA) which have been extremely conserved over the course of evolution, and which are present in eukaryotic and prokaryotic cells. Their function is to synthesize proteins by decoding the information contained in the messenger RNA. They consist of ribosomal RNAs, which carry the catalytic activity, and of ribosomal proteins. A bacterial cell has approximately 20 000 ribosomes, which are free in the cytoplasma or anchored to the cytoplasmid membrane. These particles have a sedimentation coefficient of approximately 70 Svedberg units (70S). They are composed of a small subunit (30S), which "reads" the messenger RNA, and of a large subunit (50S), which is responsible for the polymerization of the amino acids so as to form the corresponding protein. A dissociation of the 70S particles into subunits naturally occurs when the translational function performed by the ribosome bound to the mRNA comes to an end, therefore at the end of the polypeptide chains.

In the practice of the present invention, a bacterial ribosome can be obtained by any method known to those skilled in the art. The techniques for isolating bacterial ribosomes were developed in the 1960s and 1970s (Britten et al., Science, 1960, 131: 32-33; Nomura et al., "Ribosomes", Cold Spring Harbor, N.Y.: Cold Spring Harbor Laboratory; 1974) and are still widely used today with relatively minor modifications. The starting product of these techniques is a cell lysate, that is to say the product resulting from the fragmentation and disintegration of the molecular structure of the bacterial cells, carried out by physical, chemical or biological agents.

Most of the techniques for isolating ribosomes use differential ultracentrifugation or a cell lysate density gradient, which results in the isolation of the ribosomes or of the ribosomal subunits of variable purity. Crude (non-purified) ribosomes can for example be obtained by ultracentrifugation, at 100 000 g, of a cell lysate clarified at 100 000 g. The ribosome purification can be carried out by sucrose density gradient centrifugation, wherein the gradient may be continuous or batchwise; linear, exponential or logarithmic (Rivera, Maguire, and Lake, "Purification of 70S ribosomes", Cold Spring Harb Protoc, 2015, 2015(3): 300-302) Those skilled in the art know how to select the technique most suitable for obtaining ribosomes of appropriate purity.

Components of the reconstituted cell-free protein synthesis system. A reconstituted cell-free protein synthesis system contains, in addition to the bacterial ribosome, all the elements (reagents) required for the transcription reaction and for the translation reaction. Thus, a reconstituted cell-free protein synthesis system generally contains:
- the ribosome of a given bacterial species (for example *Escherichia coli*);
- transfer RNAs (tRNA) of the same bacterial species (46 tRNA in *Escherichia coli*);
- translation factors, in particular:
  - initiation factors (IF1, IF2, and IF3),
  - elongation factors (EF-G, EF-Tu, and EF-Ts),
  - termination factors (RF1, RF2, and RF3), and
  - ribosome recycling factor (RRF);
- aminoacyl-tRNA synthetases (aaRSs), which are enzymes which catalyze the binding of an amino acid to the end of the tRNA, an essential step in the translation of mRNA to proteins. In *Escherichia coli*, there are at least 20 aminoacyl-tRNA synthetases, one for each standard amino acid;
- other enzymes, in particular:
  - methionyl-tRNA transformylase (MTF), which catalyzes a reaction converting L-methionyl-tRNA into N-formylmethionyl-tRNA, which is specifically used in the initiation of protein synthesis of bacteria;
  - an exogenous RNA polymerase, typically the T7 phage (or SP6 phage or else T3 phage) RNA polymerase;
  - creatine kinase,
  - myokinase (also called adenylate kinase),
  - nucleoside-diphosphate kinase, and
  - pyrophosphatase;
- the amino acids;
- the nucleotides (ATP, GTP, CTP and UTP);
- 10-formyl-5,6,7,8-tetrahydrofolic acid (10-CHO-THF), a formyl group donor;
- buffer (for example a HEPES-KOH buffer);
- dithiothreitol (DTT); and
- salts (potassium, magnesium, ammonium, etc.).

Those skilled in the art know how to prepare or obtain the various components of a reconstituted cell-free protein system. Those skilled in the art also know how to select the amounts and respective amounts of the various components of a reconstituted cell-free protein system. An example of such amounts has been published (Ohashi et al., Pharm. Biotechnol., 2010, 11(3): 267-271; Shimizu et al., Nature Biotechnol, 2001, 19(8): 751-755).

Anti wild-type tmRNA oligonucleotide. In the commercial kits, it may be that wild-type tmRNA is inadvertently present. In particular, the present inventors have demonstrated the presence of this tmRNA in the PUREexpress® kit from New England Biolabs—presence which is not indicated by the manufacturer. This wild-type tmRNA disrupts the trans-translation reaction in the presence of the reporter system of the present invention, since it intervenes as a competitor for the modified tmRNA. In order to avoid this disruption, a reporter system for trans-translation according to the invention can also include an anti-tmRNA oligonucleotide which comprises, or consists of, a DNA sequence complementary to the DNA sequence encoding the proteolysis tag. By binding to the tmRNA at the level of the sequence encoding the proteolysis tag, the anti-tmRNA oligonucleotide prevents this contaminating tmRNA from participating in the trans-translation process.

The anti-tmRNA oligonucleotide according to the invention thus comprises, or consists of, a DNA sequence complementary to the DNA sequence encoding the proteolysis tag of the tmRNA of the bacterial species of the bacterial system for protein synthesis with which the reporter system is intended to be used.

For example, when the PUREexpress® kit from New England Biolabs is used (or more generally in the embodiments wherein the bacterial species of the ribosome and of the tRNAs used for the transcription/translation is *Escherichia coli*), the anti-tmRNA oligonucleotide may consist of the following sequence SEQ ID NO: 29: 5' GCTGCTAAAGCGTAGTTTTCGTCGTT 3'.

B. In Vivo Protein Synthesis System

In certain embodiments, the protein synthesis system is an in vivo system, that is to say a bacterial cell system. Thus, in certain embodiments, a reporter system for trans-translational activity according to the invention is used in combination with bacterial cells. As already indicated above, a reporter system for the trans-translational activity of a given bacterial species may be used with cells of the same bacterial species for a test carried out under homologous conditions. Alternatively, a reporter system for the trans-translational activity of a given bacterial species may be used with cells of a different bacterial species for a test carried out under heterologous conditions.

Bacterial cells. The invention thus also relates to the host bacterial cells comprising a construct or a vector/plasmid according to the invention. The term "bacterial cell host" or "host bacterial cell" is intended to mean herein a bacterial cell which has been transformed with a genetic construct or a vector/plasmid according to the invention. Preferably, a host bacterial cell has been transformed with a vector/plasmid containing a first DNA sequence of which the transcription produces a modified tmRNA according to the invention, and a second DNA sequence, which encodes an SmpB protein.

The bacterial cell host may be a cell from any bacterium, in particular from any bacterium that is pathogenic to human beings. In particular, the bacterial cell host may originate, without limitation, from a bacterium belonging to the genus *Staphylococcus, Micrococcus, Lactococcus, Lactobacillus, Clostridium, Bacillus, Streptococcus, Corynebacterium, Enterococcus, Listeria, Bordetella, Salmonella, Enterobacter, Klebsiella, Acinetobacter, Shigella, Yersinia, Escherichia coli, Vibrio, Pseudomonas, Neisseria, Haemophilus, Agrobacterium* or *Mycobacterium*. In particular, the bacterial cell may be a cell from: *Escherichia coli, Acinetobacter baumannii, Yersinia pestis, Vibrio cholerae, Shigella dysenteriae, Shigella flexneri, Klebsiella pneumoniae, Serratia marcescens, Enterobacter cloacae, Enterobacter aerogenes, Enterococcus faecium, Clostridium tetani, Mycobacterium tuberculosis, Mycobacterium leprae, Corynebacterium diphtheriae, Chlamydia trachomati, Borrelia burdorferi, Streptococcus pneumoniae, Streptococcus pyogenes, Pseudomonas aeruginosa, Haemophilus influenzae, Bordetella pertussis, Bordetella parapertussis, Neisseria gonorrhoeae, Neisseria meningitides, Clostridium botulinum, Treponema pallidum, Staphylococcus aureus*, or *Helicobacter pylori*.

The transformation of bacterial cells with a genetic construct or a vector/plasmid according to the invention can be carried out by any appropriate technique known to those skilled in the art. Methods for introducing expression cassettes into bacterial cells have been described, for instance transformation and conjugation; see, for example, Sambrook, Fritsch and Maniatis, *"Molecular Cloning: A Laboratory Manual"*, 1989, Cold Spring Harbor Laboratory: Cold Spring Harbor. Mention may in particular be made of the electroporation and heat shock methods. The electroporation technique consists of subjecting the bacteria in solution in the presence of the vector/plasmid to electric pulses causing pores through the wall and thus allowing the vector/plasmid to enter. In the heat shock methods, the bacteria and/or the vector/plasmid are immersed in a solution of calcium chloride, which acts on the wall of the bacteria by creating orifices. A heat shock is then applied at the same time by placing the whole mixture on ice in order to allow the vector/plasmid to come into contact with the wall, followed by the return to a temperature of 37° C. in order to ensure the introduction of said vector/plasmid into the bacterium.

Preferably, a bacterial cell host comprising a construct or a vector/plasmid according to the invention is "stably transformed". The term "stably transformed", as used herein, denotes a bacterial cell in which an exogenous nucleic acid, which was introduced by means of a transformation or conjugation method, is capable of replication. The stability of the transformation is demonstrated by the capacity of the transformed cell to establish cell lines or clones comprising a population of daughter cells which themselves also contain exogenous nucleic acid.

The success of the transformation of a bacterial cell can be evaluated, in a preliminary fashion, visually when the expression cassette or the vector/plasmid used contains a marker gene.

III—Applications of the Reporter System

The reporter system described herein can be used as a fundamental research tool for studying trans-translation, and in screening methods for identifying compounds capable of inhibiting trans-translation. The expression "capable of inhibiting trans-translation", as used herein to define or characterize a compound, denotes a compound which totally or partially reduces, curbs, prevents or prohibits transtranslational activity, this being regardless of the mechanism of action of the compound.

Screening

In general, a screening method according to the invention comprises a first step consisting in carrying out a transcription/translation in the presence of a compound to be tested and of a reporter system for trans-translation according to the invention, and a second step consisting in identifying the effect of the compound to be tested on trans-translation by detecting and/or by measuring the GFP fluorescence.

More specifically, the method for screening for compounds capable of inhibiting bacterial trans-translation comprises steps consisting in:

incubating a bacterial system for protein synthesis with a test compound;

adding, to the bacterial system for protein synthesis incubated with the test compound, a reporter system for trans-translation according to the invention; and identifying the effect of the test compound on transtranslation by detecting and/or by measuring GFP fluorescence.

Test compounds. In a screening process according to the invention, compounds of any type can be tested, Thus, a test compound can be a natural product or a synthetic product; it can be a single molecule or else a mixture or a complex of various molecules. In certain embodiments, a test compound belongs to a chemical library (that is to say a library of molecules). Chemical libraries can contain several tens to several millions of chemical compounds. Chemical libraries of natural compounds in the form of bacterial or fungal extracts, or in the form of plant extracts are available, for example, from Pan Laboratories (Bothell, Wash.) or MycoSearch (Durham, N.C.). Chemical libraries of synthetic compounds are also commercially available, for example from Comgenex (Princeton, N.J.), Brandon Associates (Merrimack, N.H.), Microsource (New Milford, Conn.), et a/drich (Milwaukee, Wis.) or from major chemical companies such as Merck, Glaxo Welcome, Bristol-Meyers-Squibb, Novartis, Monsanto/Searle, and Pharmacia UpJohn. Other examples of chemical libraries include university chemical libraries, such as the Chimiotheque Nationale Française [French National Chemical Library] (http://chimiotheque-nationale.cn.cnrs.fr/); the chemical library of the European Lead Factory (https://www.europeanleadfactory.eu/) and the chemical library of the chemical biology laboratories of UmeU in Sweden (www.chemistry.umu.se/english/research/infrastructure/lcbu/).

The test compounds can belong to any class of molecule, such as proteins, peptides, peptidomimetics, peptoids, saccharides, steroids, etc. The test compounds can also be "small molecules" or low-molecular-weight molecules, generally of between approximately 50 and approximately 2500 Daltons, for instance between 500 and 700 Daltons, or less than 350 Daltons.

In certain embodiments, the biological activity of the test compounds is not known. In particular, it is not known whether these compounds have antibacterial activity. In others, the compounds to be tested are known to demonstrate antibacterial activity, but their mechanism of action is not well known or is unknown.

A screening process according to the invention can be used to search for combinations of therapeutic agents, for example to demonstrate the synergistic effects of a known therapeutic agent with a test compound (or else with another known therapeutic agent).

Incubation. The first step, which consists in carrying out a transcription/translation in the presence of a test compound and of a reporter system for trans-translation according to the invention, comprises the incubation of the test compound with a bacterial system for protein synthesis (in vitro or in vivo—see above).

The incubation in a screening method according to the invention can be carried out by any appropriate method. Thus, a test compound can be incubated with a bacterial system for protein synthesis on or in any appropriate support and in particular on a plate, in a tube or a flask, on a membrane, or on a gelled support, etc. In certain embodiments, the incubation is carried out in a multiwall plate, which makes it possible to carry out, in parallel, numerous and varied assays. Among the typical supports are microtitration plates and more particularly 12-well, 24-well, 48-well, 96-well, 384-well (or more) plates, which are easy to handle.

In a screening process according to the invention, the incubation of the bacterial system for protein synthesis (in vitro or in vivo) with a test compound can be carried out under any appropriate conditions (temperature, humidity, pH, salinity, etc.). The concentration of test compound during the incubation can be adjusted according to the type of compound (its toxicity, its hydrophobicity, etc.), the amount of bacterial system for protein synthesis (for example, the number of bacterial cells or the amount of bacterial ribosome), the duration of the incubation period, etc. Generally, in a screening method, the bacterial system for protein synthesis is exposed to test compound concentrations ranging from approximately 1 fM to approximately 10 mM. Preferably, the concentrations used are between approximately 10 pM and approximately 100 µM. It is of course possible to test other concentrations without deviating from the present invention. Each compound can, furthermore, be tested, in parallel, at various concentrations. The incubation can be maintained for any appropriate duration, for example between a few minutes and several hours or days, for example between 5 and 72 hours.

According to the support and the nature of the test compound, variable amounts of bacterial system for protein synthesis (in vitro or in vivo) can be used during the implementation of the screening processes described herein. Conventionally, in the embodiments wherein the bacterial system for protein synthesis is an in vivo system, $10^3$ to $10^6$ cells are incubated with a test compound, preferentially between $10^4$ and $10^5$ cells. In the embodiments wherein the bacterial system for protein synthesis is an in vitro system containing a ribosome, the ribosome is incubated at a concentration of between 0.1 µM and 10 µM, preferably between 0.5 µM and 3 µM.

One or more (positive or negative) control compounds can be used for evaluating, by comparison, the effects of the test compound on the trans-translation.

Transcription/Translation. A reporter system for trans-translation according to the invention is then added to the protein bacterial system incubated with the test compound, so as to carry out the reaction of transcription/translation of the nucleotide sequence encoding the first 10 domains of GFP and not comprising a stop codon, which results in a stalled ribosome and the wild-type (trans-translation) reaction by SmpB and the modified tmRNA of the reporter system.

Detection/Measurement of the fluorescence of the reassembled GFP. In a screening process according to the invention, the effect of the test compound on the trans-translation is identified by detecting and/or by measuring GFP fluorescence. The measurement (or quantification) of the GFP fluorescence can be carried out by any fluorescence technique: such as spectrofluorometry, fluorescence microscopy, the reading of fluorescence in plates, etc.

Identification of trans-translation-inhibiting compounds. In a screening process according to the invention, a test compound is identified as a compound capable of inhibiting trans-translation if there is no (or little) addition of the $11^{th}$ domain of GFP to the incomplete protein blocked in the ribosome, and therefore no (or little) formation of complete GFP, which results in an absence of or a weak fluorescence intensity. The detection of the fluorescence or the measurement of the fluorescence intensity in the presence of the test compound can be compared with the detection of the fluorescence or the measurement of the fluorescence intensity in the absence of the test compound. The detection of the fluorescence or the measurement of the fluorescence intensity in the presence of the test compound can alternatively or also be compared with the detection of the fluorescence or the measurement of the fluorescence intensity in the presence of a positive or negative control.

Development of antibiotics. A screening process according to the invention has the objective of identifying compounds capable of being of interest as antibiotics.

A screening test according to the invention can be followed by other assays, for example by one or more screening tests according to the invention carried out on other species of bacteria. Alternatively or additionally, a screening test according to the invention can be followed by in vivo toxicity studies on cell models or animal models of bacterial infections. The antibacterial activity can be verified by the study of bacterial growth, by producing antibiograms and the study of the Minimum Inhibitory Concentrations/Minimum Bactericidal Concentrations (MIC/MBC).

When a test compound has been identified as having a specific or predominant anti-trans-translation action, studies of structure-activity relationships can be carried out with the objective of identifying new antibiotic backbones having improved properties compared with the test compound identified and of developing new therapeutic strategies beyond the known bacterial multiresistances.

The invention also relates to the compounds identified by means of a screening method according to the invention or the derivatives thereof, and also any pharmaceutical composition comprising at least one compound identified by a screening method according to the invention or a derivative thereof. A pharmaceutical composition according to the invention comprises at least one compound identified by means of a screening method according to the invention or a derivative thereof and at least one physiologically acceptable carrier or excipient. In the context of the present invention, the expression "physiologically acceptable carrier or excipient" is intended to mean any medium or additive which does not interfere with the efficacy of the biological activity of the active ingredient and which is not excessively toxic to the patient or subject, under the conditions in which it is administered. Preferably, the physiologically acceptable carrier or excipient is suitable for human pharmaceutical use.

The invention also relates to the use of these compounds, derivatives and/or pharmaceutical compositions as antibiotics. The present invention also relates to a method for treating a disease of bacterial origin, comprising a step consisting in administering, to a patient or a subject, an effective amount of a compound or of a derivative or of a pharmaceutical composition comprising such a compound or derivative. This method can, in particular, be used for the treatment of a bacterial infection, such as an infection caused by a Gram+ pathogenic bacterium or by a Gram− pathogenic bacterium or by a mycobacterium. In the context of the present invention, the term "treatment" is intended to mean a method which has the objective (1) of delaying or preventing the beginning of a disease or of a clinical condition; (2) of delaying or stopping the progression, the worsening and/or the deterioration of the symptoms of the disease; (3) of bringing improvements in the symptoms of the disease; and/or (4) of curing the disease. A treatment can be administered before the beginning of the disease for a preventive action, or it can be administered after initiation of the disease, for a therapeutic action. The term "subject" denotes herein a mammal, whereas the term "patient" is preferably used when the subject is a human being. A compound identified by a screening method according to the invention (or a derivative thereof or a pharmaceutical composition comprising such a compound or derivative) can be administered by any suitable route of administration (oral, parenteral, rectal, pulmonary, nasal, cutaneous, transdermal, mucosal, etc.) and may be local or systemic. The optimal route of administration can be determined according to the nature and/or the location of the bacterial infection.

The bacterial infections which can be treated by administering a compound identified by a screening method according to the invention, or a derivative thereof, include, without limitation, bacterial urinary infections, bacterial skin infections, bacterial intestinal infections, bacterial pulmonary infections, bacterial osteoarticular infections, bacterial genital infections, bacterial dental infections, septicemia, nosocomial infections, bacterial meningitis, bacterial gastroenteritis, endocarditis, endocarditis pneumonia, bacterial anginas, bacterial otitis, salmonella infections, etc. In particular, a compound identified by a screening method according to the invention, or a derivative thereof, can be used for treating tuberculosis (which is caused by the bacterium *Mycobacterium tuberculosis*), leprosy (caused by *Mycobacterium leprae*), the plague (caused by *Yersinia pestis*), cholera (caused by *Vibrio cholerae*), tetanus (caused by *Clostridium tetani*), botulism (caused by *Clostridium botulinum*), diphtheria (caused by *Corynebacterium diphtheriae*), dysentery (caused by *Shigella dysenteriae*), chlamydia (caused by *Chlamydia trachomatis*), gonorrhea (caused by *Neisseria gonorrhoeae*), meningitis (caused by *Neisseria meningitides* or by *Haemophilus influenzae*), syphilis (caused by *Treponema pallidum*), Lyme disease (caused by *Borrelia burdorferi*), whooping cough (caused by *Borrelia parapertussis*), gastroduodenal ulcer (caused by *Helicobacter pylori*), pneumonia (caused by *Streptococcus pneumoniae* or by *Streptococcus pyogenes*), infections caused by *Staphylococcus aureus*, such as toxic shock syndrome, and opportunistic and nocosomial infections caused by *Pseudomonas aeruginosa, Klebsiella pneumoniae, Serratia marcescens* or *Enterobacter aerogenes*.

In certain particular embodiments of the invention, a compound identified by a screening method according to the invention, or a derivative thereof, can be used for treating an infection caused by one of the bacteria termed ESKAPE, which represent the most significant threat—in particular in health premises—since they rapidly become resistant to several classes of antibiotics. The "ESKAPE" bacteria comprise *Enterococcus faecium, Staphylococcus aureus*, species of the genus *Klebsiella, Acinetobacter baumannii, Pseudomonas aeruginosa* and the *Enterobacter* species.

IV—Kits

The present invention is also directed towards kits comprising material that is of use for carrying out a method according to the invention. In particular, the present invention relates to kits for the fundamental study of trans-translational activity and kits for screening for compounds capable of inhibiting trans-translation in at least one bacterial species or strain.

In general, a kit according to the invention comprises a reporter system for trans-translation, comprising the three main components, namely:
- a nucleotide sequence encoding the first 10 domains of GFP and not comprising a stop codon;
- the SmpB protein of said bacterial species, or a biologically active fragment of this protein or a DNA sequence encoding this protein or this fragment; and
- a modified tmRNA corresponding to the tmRNA of said bacterial species, of which the portion of sequence encoding the peptide label is replaced with a sequence encoding the 11$^{th}$ domain of GFP, or a DNA sequence encoding this modified tmRNA.

As previously indicated, the components of the reporter system for trans-translation can be inserted into one and the same plasmid or into two separate plasmids.

In certain embodiments, a kit can also comprise an anti-wild-type tmRNA oligonucleotide, as defined above.

In certain embodiments, a kit according to the invention can also comprise all or some of the components of a reconstituted cell-free protein synthesis system, as listed above.

In other embodiments, a kit according to the invention can comprise bacterial cells intended to be transformed with a vector/plasmid contained in the kit and comprising a DNA sequence encoding the SmpB protein and a sequence encoding the modified tmRNA according to the invention. Alternatively, a kit can comprise bacterial cells already transformed with such a vector/plasmid.

A kit according to the invention can also comprise reagents or solutions for carrying out a screening method according to the invention, for example reagents or solutions for transforming bacterial cells with a vector/plasmid according to the invention, reagents or solutions for culturing such cells in liquid solution, on gel or in a biofilm, reagents or solutions for incubating a test compound, reagents or solutions for incubating the bacterial system for protein synthesis, positive and/or negative controls of trans-translation, etc. Protocols for using these reagents and/or solutions can also be included in the kit.

The various components of the kit can be provided in solid form (for example in freeze-dried form) or in liquid form. A kit can optionally comprise a receptacle containing each of the reagents or solutions, and/or receptacles for carrying out certain steps of the screening process of the invention.

A kit according to the invention can also comprise instructions for carrying out a screening method according to the invention.

A kit according to the invention can also comprise a leaflet in the form recommended by a governmental agency regulating the preparation, sale and use of biological products.

Unless otherwise defined, all the technical and scientific terms used herein have the same meaning as that commonly understood by an ordinary specialist in the field to which this invention belongs. Likewise, all the publications, patent applications, all the patents and other references mentioned herein are incorporated by way of reference.

EXAMPLES

The following examples describe certain embodiments of the present invention. However, it is understood that the examples are presented only by way of illustration and do not in any way limit the scope of the invention. The examples presented below have been described in a scientific article (Guyomar et al., "Reassembling GFP to Evaluate Trans-Translation in vitro") submitted for review at the beginning of June 2018.

Introduction

In order to explore the use of trans-translation as a target for the development of antibiotics, the present inventors designed and developed a fluorescent reporter system, in which the mechanism is monitored by the fluorescence intensity of a reconstituted green fluorescent protein (GFP). The test is based on the reassembly of an active "Superfolder" GFP (sfGFP) after labeling with a modified tmRNA.

Indeed, semi-synthetic green fluorescent proteins (GFP), such as the GFP variant known as "superfolder" (Cabantous et al., Nature Methods, 2006, 3(10): 845-854), consist of eleven domains which can be assembled by adding a short fragment to a truncated protein, in a method known as split GFP (Kent et al., J. Am. Chem. Soc., 2008, 130(30): 9664-9665). This method is based on breaking between the 10$^{th}$ β-domain and the 11$^{th}$ β-domain of GFP. The resulting two fragments, GFP1-10 and GFP11, wherein GFP11 is a short peptide of 16 amino acids, can be easily reassembled (Kamiyama et al., Nature Commun., 2016, 7: 11046). The GFP1-10 is non-fluorescent by itself, but recovers complete fluorescence during the complementation with the GFP11 fragment, which results in maturation of the chromophores in the reconstituted functional GFP.

In the method of the present invention, the missing GFP domain is covalently added to a non-stop GFP1-10 fragment by means of a manipulated trans-translation process and not simply added by self-complementation (see FIG. 1). With this aim, the present inventors designed a variant of the tmRNA in which the sequence of the MLD encoding the sequence specifically recognized by the proteases was replaced with the sequence encoding GFP11 (ARDHMVL-HEYVNAAGIT—SEQ ID NO: 18, see FIG. 2), followed by a stop codon. The nucleotides upstream of the resume codon and also the alanine resume codon of the original sequence were conserved since they play an instrumental role during the re-registration of the tag reading frame (Kapoor et al., J. Bacteriol., 2011, 193(14): 3569-3576). In order to minimize the disruption of the RNA structure, compensatory mutations were also produced (see FIG. 2(B), dark green) in order to maintain the base pairing interactions in the H5 helix which incorporates the 3' end of the MLD (see FIG. 2(A)). This modified tmRNA is called "$tmRNA_{GFP11}$".

In order to evaluate the tmRNA labeling activity in vitro, the present inventors used a reconstituted cell-free protein synthesis system (PURE for Protein Synthesis Using Recombinant Elements) (Shimizu et al., Nature Biotechnol., 2001, 19(8): 751-755). The experiments were carried out using the PURExpress® commercial kit (sold by New England Biolabs) containing all the purified components of *Escherichia coli* that are required to carry out both the transcription and the translation. In order to convert this kit into an in vitro fluorescent trans-translation system, the inventors added the components required for the trans-translation: $tmRNA_{GFP11}$, the SmpB protein, and a non-stop DNA sequence encoding the first 10 domains of sfGFP (see Materials and Methods section).

Materials and Methods

Plasmid constructs. The gene encoding the $tmRNA_{GFP11}$ was obtained by site-directed mutagenesis using the pGEMEX-tmRNA plasmid (Takahashi et al., J. Biol. Chem., 2003, 278(30): 27672-27680) as template and the primers 1 and 2 (SEQ ID NO: 31 and SEQ ID NO: 32, respectively, see Table 1 below). Thus, the specific sequence recognized by the proteases (SEQ ID NO: 30: ANDENYALAA) was replaced with a sequence consisting of the sequence SEQ ID NO: 18: ARDHMVLHEYVNAAGIT (which contains the conserved first alanine of the native tmRNA plus the sequence encoding the 11$^{th}$ domain of sfGFP), and also compensatory mutations for the H5 helix (see FIG. 2). The fragment thus obtained was then inserted between the NdeI and HindIII sites of the pGEMEX plasmid so as to generate pGEMEX-mtmRNA$_{GFP11}$. From this first plasmid, the pBstNav-mtmRNA$_{GFP11}$ and pUC19mtmRNA$_{GFP11}$ plasmids were respectively constructed for the in vitro production and the in vivo production. The inventors firstly amplified the tmRNA$_{GFP11}$ sequence with the primers 3 and 4 (SEQ ID NO: 33 and SEQ ID NO: 34, respectively, see Table 1 below) on the pGEMEX-mtmRNA$_{GFP11}$ plasmid, and cloned the resulting sequence into the pBstNav vector between EcoRI and PstI restriction sites. Secondly, the inventors amplified the same tmRNA$_{GFP11}$ sequence with the primers 5 and 6 (SEQ ID NO: 35 and SEQ ID NO: 36, respectively, see Table 1 below) and cloned it between the HindIII and BamHI restriction sites in the pUC19 vector so as to generate the pUC19mtmRNA$_{GFP11}$ plasmid.

The smpB gene was amplified from the *E. coli* genome using the primers 10 and 11 (SEQ ID NO: 40 and SEQ ID NO: 41, respectively, see Table 1) and inserted into the pET-22(b)+ (Amp$^R$) vector between the NdeI and XhoI restriction sites. The resulting plasmid, called pF1275, was verified by sequencing. It allows the production of the SmpB protein labeled with a His-tag in the C-terminal portion, under the control of the T7 promoter. The pQE30 plasmid allows the production of the His-tag alanyl-tRNA synthetase (AlaRS) protein, the gene of which is inserted between the SphI and HindIII restriction sites (Shimizu et al., Nature Biotechnol., 2001, 19(8): 751-755).

TABLE 1

Primers used.

| No. | Primer | SEQ ID NO | Sequence |
|---|---|---|---|
| 1 | GFP11hélix forward | SEQ ID No.: 31 | 5'ACCCAAGGTGCATGCCGAGGGGCGGT TGGCCTCGTAAAAAGCCGCAAAAAATA GTCGCACGTGACCACATGGTCCTTCATG AGTACGTAAATGCTGCTGGGATTACATA ATAACCTAATCCTAGCCCTCTCTCCCTA GC 3' |
| 2 | GFP11hélix reverse | SEQ ID No.: 32 | 5' TAGAATACTCAAGCTTCGCG 3' |
| 3 | tmGFP11_BstNav_forward | SEQ ID No.: 33 | 5'AAAAGAATTCGGGGCTGATTCTGGATT CGAC 3' |
| 4 | tmGFP11_BstNav_reverse | SEQ ID No.: 34 | 5'AAGGCTGCAGTGGTGGAGCTGGCGGG AG TTG 3' |
| 5 | pUC19_tm11_forward | SEQ ID No.: 35 | 5'GGAAGCTTAATACGACTCACTATAGG GG CTGATTCTGGATTC 3' |
| 6 | pUC19_tm11_reverse | SEQ ID No.: 36 | 5'GGGGATCCCGTCTCCTGGTGGAGCTGG C GGGA 3' |
| 7 | GFPfold for | SEQ ID No.: 37 | 5' CTCGATCCCGCGAAATTAATACG 3' |
| 8 | GFP1-10nonSTOP rev | SEQ ID No.: 38 | 5' CTTTTCGTTGGGATCTTTCG 3' |

TABLE 1-continued

Primers used.

| No. | Primer | SEQ ID NO | Sequence |
|---|---|---|---|
| 9 | alaGFPfold rev | SEQ ID No.: 39 | 5'CCGGCCTAGGTTATGTAATCCCAGCAG CATTTACGTACTCATGAAGGACCATGTG GTCACGTGCCTTTTCGTTGGGATCTTTC GAAAG 3' |
| 10 | smpB_forward | SEQ ID No.: 40 | 5' TCACGACGCATATGACGAAG 3' |
| 11 | smpB_reverse | SEQ ID No.: 41 | 5' TCGAGACGGTGGGCGTTTTC 3' |

Protein Purifications

The SmpB. protein. The His-labeled SmpB protein was expressed using the pF1275 vector under the control of a T7 promoter in BL21(DE3)ΔssrA cells (Cougot et al., J. Mol. Biol., 2014, 426(2): 377-388). The cultures were carried out in Lysogeny LB culture broth supplemented with ampicillin (100 µg/ml) and with kanamycin (50 µg/ml). The expression of the protein was induced in an exponential phase ($DO_{600\ nm}$ 0.5) with 0.1 mM of isopropyl-ß-D-1-thiogalactopyranoside (IPTG) overnight at 16° C. The cells were centrifuged, washed and resuspended in lysis buffer (50 mM Hepes-KOH, pH 7.5, 200 mM KCl, 20 mM imidazole, 1 mM DTT). The cell lysis was carried out using a "French press". The lysate was centrifuged, and the supernatant was filtered (0.2 pm) and injected onto an Ni-NTA Sepharose column (HisTrap FF, GE Healthcare Life Sciences) pre-equilibrated with the lysis buffer. The column was washed with 100 ml of lysis buffer and 50 ml of washing buffer (50 mM Hepes-KOH, pH 7.5, 200 mM KCl, 1 M NH4Cl, 20 mM imidazole, 1 mM DTT) before elution with 500 mM of imidazole. The fractions containing pure SmpB were concentrated using the Amicon 10 KDa purification system and by replacing the buffer with a concentrating buffer (50 mM Hepes-KOH, pH 7.5, 100 mM KCl, 1 mM dithiotreitol DTT and 10% glycerol).

AlaRS. The His-tag alanyl-tRNA synthetase (AlaRS) protein was purified in the same way as the SmpB protein. A final concentration of 1 mM of IPTG was used to induce the production of the protein for 4 hours at 37° C. The buffers used for this purification are the lysis buffer (50 mM $NaH_2PO_4/Na_2HPO_4$, 500 mM NaCl, 10 mM imidazole and 10% glycerol at pH 7.4), the washing buffer (50 mM $NaH_2PO_4/Na_2HPO_4$, 500 mM NaCl, 30 mM imidazole and 10% glycerol at pH 7.4), the elution buffer (50 mM $NaH_2PO_4/Na_2HPO_4$, 500 mM NaCl, 50.0 mM imidazole and 10% glycerol at pH 7.4) and, finally, the concentrating buffer (60 mM Tris-HCl, pH 7.5, 10 mM $MgCl_2$, 50% glycerol and 10 mM DTT) in order to concentrate and dialyze the protein (Amicon 100 KDa).

Purification of the $tmRNA_{GFP11}$ in vivo. The $tmRNA_{GFP11}$ was produced in vivo in the E. coli JM101tr strain. After extraction with phenol/chloroform, the $tmRNA_{GFP11}$ was purified under natural conditions, as previously described (Ranaei-Siadat et al., RNA, 2014, 2(10): 1607-1620). The RNA molecule was first separated from the RNA pool in two steps, using Resource Q™ (GE Healthcare) and Mono Q™ (GE Healthcare) columns pre-equilibrated with 20 mM potassium phosphate buffer, pH 6.5-1 mM EDTA, and using an NaCl gradient. The purity of the samples was then improved on a Superdex 200™ (GE Healthcare) in 20 mM potassium phosphate, pH 6.5, 2 mM EDTA, 150 mM NaCl buffer. The $tmRNA_{GFP11}$ was eluted in the form of a monomer.

Purification of the $tmRNA_{GFP11}$ in vitro. The $tmRNA_{GFP11}$ was produced in vitro using the $pUC19mtmRNA_{GFP11}$ plasmid. Ten (10) µg of plasmid were digested with the BsmBI restriction enzyme (to generate the 3' CCACCA required for the aminoacylation) and the DNA was purified using a phenol/chloroform mixture. The digested and purified plasmid was then precipitated and the resultant pellet was resuspended in 40 µL of nuclease-free water overnight. The MEGAscript™ T7 transcription kit (from ThermoFisher Scientific) was used to transcribe the $tmRNA_{GFP11}$, then it was purified using the MEGAclear™ purification kit for large-scale transcription reactions (Life Technologies).

DNA template and oligonucleotide production. The GFP1-10 nonstop sequence was produced by PCR using the primers 7 and 8 (SEQ ID NO: 37 and SEQ ID NO: 38, respectively, see Table 1) and the pETGFP 1-10 vector as template for the trans-translation assays, for blocking the 70S ribosomes (the pETGFP 1-10 vector was generously provided by Dr. Stephanie Cabantous of the Institut de Pharmacologie et biologie structural [Institute for Pharmacology and Structural Biology], Toulouse, France). Likewise, the primers 7 and 9 (SEQ ID NO: 37 and SEQ ID NO: 39, respectively, see Table 1) were used to amplify the alaGFP superfolder. The two PCR products have a T7 promoter upstream of the coding sequence.

Translation and trans-translation assays. The in vitro translation reactions were carried out according to the recommendations of New England Biolabs. The in vitro trans-translation assays were carried out in various steps using the PURExpress® protein synthesis kit (New England Biolabs). The first step consists of a folding of the $tmRNA_{GFP11}$ (50 pmol per reaction). An incubation at 80° C. in a folding buffer (5 mM $MgCl_2$, 20 mM $NH_4Cl$ and 10 mM Hepes-KOH, pH 7.5) is followed by a second incubation at ambient temperature for 30 minutes. The second step is the aminoacylation of the $tmRNA_{GFP11}$: 50 pmol of folded $tmRNA_{GFP11}$ are incubated with 50 pmol of SmpB, 75 pmol of AlaRS, 2.5 mM of ATP and 30 mM of alanine for 30 minutes at 37° C. The 70S ribosomes originating from the PURExpress® kit are then blocked by adding 250 ng of purified PCR product encoding sfGFP1-10 nonstop under the control of the T7 promoter. During this step, 5 µM of anti-ssrA nucleotide (see Table 2) are added in order to neutralize the native tmRNA present in the kit. Finally, the blocked ribosomes and the aminoacylated $tmRNA_{GFP11}$ were reassembled with a further 50 pmol of SmpB (for a final amount of 100 pM) for an overnight incubation at 37° C. (in a thermocycle).

TABLE 2

Antisense oligonucleotides used.

| Oligonucleotide | SEQ ID No. | Sequence |
|---|---|---|
| anti-ssrA (or anti-tmRNA) | SEQ ID No.: 29 | 5'GCTGCTAAAGCGTAGTTTTCGTCGTT 3' |
| anti-ssrAGFP11 | SEQ ID No.: 42 | 5'CCCAGCAGCATTTACGTACTCATGAAGGACCATG TGGTCAC 3' |

Analysis by fluorescence. After overnight incubation at 37° C., the reaction volume was adjusted to 125 μL and transferred into a cuvette for analysis by fluorescence using an LS 55 fluorescence spectrometer (Perkin Elmer). The fluorescence intensity at 510 nm of the trans-translated sfalaGFP was determined using an excitation at 485 nm.

Results

The inventors first of all confirmed that there was no fluorescence generated by the components of the PURExpress® kit (see FIG. 3). As described above, the inventors conserved the first alanine resume codon: in the tmRNA$_{GFP11}$. Consequently, if the trans-translation is active, an alanine is added to sfGFP, just upstream of the 11$^{th}$ domain of GFP. Consequently, the inventors made sure that the PURE system enabled the synthesis of a functional sfGFP (that is to say fluorescent sfGFP), despite the presence of this additional alanine between the sfGFP1-10 and sfGFP11 domains (see FIG. 3(A)). This GFP was called "sfalaGFP". With this aim, the inventors used a purified PCR product as template DNA, with the gene encoding sfalaGFP under the control of a T7 promoter. The sequence of the sfalaGFP PCR product (SEQ ID NO: 43 below) to produce the superfolder GFP with an additional alanine (in italics, in bold and underlined) before domain 11 of GFP (the T7 promoter is underlined, the RBS sequence is in bold, the first codon and the stop codon are underlined and in bold)

5'CTCGATCCCGCGAAATTAATACGACTCACTATAGGGGAATTGTGAGCG

GATAACAATTCCCCTCTAGAAATAATTTTGTTTAACTTTAAGAAGGAGAT

ATACATATGGGTGGCACTAGTAGCAAAGGAGAAGAACTTTTCACTGGAGT

TGTCCCAATTCTTGTTGAATTAGATGGTGATGTTAATGGGCACAAATTTT

CTGTCAGAGGAGAGGGTGAAGGTGATGCTACAATCGGAAAACTCACCCTT

AAATTTATTTGCACTACTGGAAAACTACCTGTTCCATGGCCAACACTTGT

CACTACTCTGACCTATGGTGTTCAATGCTTTTCCCGTTATCCGGATCACA

TGAAAAGGCATGACTTTTTCAAGAGTGCCATGCCCGAAGGTTATGTACAG

GAACGCACTATATCTTTCAAAGATGACGGGAAATACAAGACGCGTGCTGT

AGTCAAGTTTGAAGGTGATACCCTTGTTAATCGTATCGAGTTAAAGGGTA

CTGATTTTAAAGAAGATGGAAACATTCTCGGACACAAACTCGAGTACAAC

TTTAACTCACACAATGTATACATCACGGCAGACAAACAAAAGAATGGAAT

CAAAGCTAACTTCACAGTTCGCCACAACGTTGAAGATGGTTCCGTTCAAC

TAGCAGACCATTATCAACAAAATACTCCAATTGGCGATGGCCCTGTCCTT

TTACCAGACAACCATTACCTGTCGACACAAACTGTCCTTTCGAAAGATCC

CAACGAAAAG*GCA*CGTGACCACATGGTCCTTCATGAGTACGTAAATGCTG

CTGGGATTACATAACCTAGGCCGG3'

In the same way, the inventors verified that the first 10 translated domains of sfGFP1-10 did not exhibit fluorescence (see FIG. 3(A)).

The results obtained show a strong fluorescent signal for the production of sfalaGFP, indicating that the template DNA has indeed been transcribed and translated, but also that the fluorescent protein was indeed folded and functional. No inhibition of transcription and of translation was observed with anti-translation controls, such as KKL-35 (see FIG. 3(A)).

Secondly, in order to synthesize an sfGFP1-10 protein blocked on the ribosome, the inventors added, to the PURExpress® system, a PCR product encoding sfGFP1-10 under the control of a T7 promoter and devoid of a stop codon. The diagram of FIG. 1 represents the approach used, beginning with the ribosome stored on a non-stop messenger RNA. In order to recycle the two ribosome subunits, the complex consisting of alanyl-tmRNA$_{GFP11}$ and of SmpB is added to the reaction. The complex is housed in the ribosome and the translation resumes on the MLD of tmRNA$_{GFP11}$. Consequently, the 11$^{th}$ domain is added to sfGFP1-10 by trans-translation and a functional sfalaGFP is released (see FIG. 1). It should be noted that, in order to avoid any interfering trans-translation activity due to the presence of native mRNA in the PURExpress kit, which was demonstrated by the present inventors, an anti-ssrA oligonucleotide targeting the wild-type tmRNA and not the tmRNA$_{GFP11}$ was added to all the reactions (see Table 2 and Materials and Methods).

FIG. 3(B) shows the percentage fluorescence measured for the trans-translation assays. As negative control, all the components of the system were added, with the exception of the tmRNA$_{GFP11}$. Contrary to this negative control, the addition of tmRNA$_{GFP11}$ induces a trans-translation of sfalaGFP and an increase in the fluorescence signal by a factor of 16 (see FIG. 3(B)). Various molecules were then used as trans-translation inhibitors: an antisense oligonucleotide targeting the tmRNA$_{GFP11}$, called anti-ssrAGFP11 (SEQ ID NO 42, Table 2), and the chemical compound KKL-35, known to have strong anti-translation activity (Ramadoss et al., PNAS USA, 2013, 110(25): 10282-10287). As shown from FIG. 3, the addition of the anti-tmRNA$_{GFP11}$ oligonucleotide decreases the fluorescence intensities by more than 12 times. This demonstrates the strong anti-trans-translation activity of the antisense. For its part, KKL-35 has a slight activity against the trans-translation at a concentration of 10 μM. This is not surprising when account is taken of the fact that KKL-35 and other oxadiazole compounds certainly have targets other than trans-translation in vivo (Macé et al., J. Mol. Biol., 2017, 429(23): 3617-3625; Brunel et al., Antimicrob. Agents Chemother., 2018, 62(2): e01459-17).

The system developed by the present inventors is a powerful tool for identifying trans-translation inhibitors in vitro (that is to say in a cell-free medium). It allows rapid and precise detection of trans-translation by fluorescence spectrometry. In addition, it facilitates the preparation of ribosome-tmRNA-SmpB complexes for understanding the mechanism of trans-translation by structural studies. The system is non-radioactive and transposable in vivo (that is to say in a medium comprising bacterial cells). In addition to its rapidity, it is also optimized for the high-throughput screening of chemical compounds in 96-well black microplates using microplate fluorimetry.

SEQUENCE LISTING

```
<160> NUMBER OF SEQ ID NOS: 43

<210> SEQ ID NO 1
<211> LENGTH: 758
<212> TYPE: DNA
<213> ORGANISM: Artificial Sequence
<220> FEATURE:
<223> OTHER INFORMATION: Synthetic Nucleotidic sequence for the 10 first
      domains of the GFP and not comprising stop codon, functionally
      linked, in the 5' position, to a T7 promotor, and to an initiation
      site corresponding to an RBS ribosome-binding site

<400> SEQUENCE: 1
ctcgatcccg cgaaattaat acgactcact atagggggaat tgtgagcgga taacaattcc      60
cctctagaaa taattttgtt taactttaag aaggagatat acatatgggt ggcactagta     120
gcaaaggaga agaactttc actggagttg tcccaattct tgttgaatta gatggtgatg      180
ttaatgggca caaatttct gtcagaggag agggtgaagg tgatgctaca atcggaaaac      240
tcacccttaa atttatttgc actactgaa aactacctgt tccatggcca cacttgtca       300 ctactctgac ctatggtgtt caatgctttt cccgttatcc ggatcacatg aaaaggcatg     360
actttttcaa gagtgccatg cccgaaggtt atgtacagga acgcactata tctttcaaag     420
atgacgggaa atacaagacg cgtgctgtag tcaagtttga aggtgatacc cttgttaatc     480
gtatcgagtt aaagggtact gatttaaag aagatggaaa cattctcgga cacaaactcg      540
agtacaactt taactcacac aatgtataca tcacggcaga caaacaaaag aatggaatca     600
aagctaactt cacagttcgc cacaacgttg aagatggttc cgttcaacta gcagaccatt     660
atcaacaaaa tactccaatt ggcgatggcc ctgtcctttt accagacaac cattacctgt     720
cgacacaaac tgtcctttcg aaagatccca acgaaaag                             758

<210> SEQ ID NO 2
<211> LENGTH: 483
<212> TYPE: DNA
<213> ORGANISM: Escherichia coli

<400> SEQUENCE: 2
atgacgaaga aaaagcaca taaacctggt tcagcgacca tcgcgcttaa caagcgcgcc      60
cgtcacgaat actttatcga agaagagttc gaagcgggac ttgccctgca aggctgggaa     120
gttaaatccc tgcgcgcagg aaaagccaat atcagcgaca gctacgtcct tctgcgtgac     180
ggagaggcat ttctgtttgg cgctaacatc acgccaatgg ccgtggcctc cacgcatgtg     240
gtgtgcgatc ctacccgtac ccgcaagtta cttctcaacc agcgcgaact ggactcattg     300
tacggtcgcg tcaatcgaga aggctatacc gtagtggcgc tctccctgta ctggaaaaat     360
gcctggtgca aagtgaaaat cggcgtcgcc aaaggtaaga acagcacga taaacgttca     420 gatatcaaag agcgcgaatg gcaggtggat aaagcacgta tcatgaaaaa cgcccaccgt     480
taa                                                                  483

<210> SEQ ID NO 3
<211> LENGTH: 465
<212> TYPE: DNA
<213> ORGANISM: Enterococcus faecium
```

<400> SEQUENCE: 3

```
atgccaaaag gcgagggaaa attaattgca caaaacaaga aagctcgcca tgattattcg    60
atcatcgaca cgatggaagc agggatggtc ttgcaaggaa ccgagatcaa gtcgatacga   120
aacagccgga tcaatctaaa agatggattt attcgcgtcc gcaacggaga agctttcttg   180
cataatgttc atatcagtcc ttatgaacaa ggaaatattt ttaatcatga tccgttgcgc   240
acgagaaagt tattattaca caaaaaacaa atcatccggc ttgaaaatga attgaaaaat   300
actggaatca ctgttgttcc tttaaaagtc tatattcgta acggctatgc caaggtattg   360
attggtctgg cgaaagggaa aaaatcttat gataaacggg aagatttgaa acgaaaagat   420
atcgatcgac aaattgatcg aacattaaaa aatttctcta gataa                   465
```

<210> SEQ ID NO 4
<211> LENGTH: 465
<212> TYPE: DNA
<213> ORGANISM: Staphylococcus aureus

<400> SEQUENCE: 4

```
atggctaaga agaaatcacc aggtacatta gcggaaaatc gtaaagcaag acatgattat    60
aatattgaag acacgattga agcgggaatc gtattacaag gtacagaaat aaaatcgatt   120
cgccgaggta gtgctaacct aaagatagt tacgcgcaag ttaaaaacgg tgaaatgtat   180
ttgaataata tgcatatagc accatacgaa aagggaatcg ttttaatca cgatcctctt   240
cgttctcgaa aattattatt gcataaacgt gaaatcatta aattgggtga tcaaacacgt   300
gaaattggtt attcgattgt gccattaaag ctttatttga agcatgggca ttgtaaagta   360
ttacttggtg tcgcacgagg taagaaaaaa tatgataaac gtcaagcttt gaaagaaaaa   420
gcagtcaaac gagatgttgc gcgcgatatg aaagcccgtt attaa                   465
```

<210> SEQ ID NO 5
<211> LENGTH: 483
<212> TYPE: DNA
<213> ORGANISM: Klebsiella pneumoniae

<400> SEQUENCE: 5

```
atgactaaga aaaagcccca caaacctgga tcagccacca ttgcgctgaa taaacgcgcc    60
cgtcacgaat actttatcga agatgaatac gaggctggtc tcgccctgca gggctgggaa   120
gtcaaatccc tgcgtgcagg caaagccaac atcggcgata gctatgtcat cctgaaggat   180
ggcgaagcct tcctgttcgg cgccaacttt acgcccatgg ccgtggcttc cacccactat   240
gtctgcgacc cgacgcgcac ccgtaagctg ctgctcaacc agcgtgagct ggacacgctg   300
tacgccgcca ttaaccgcga aggttacacc gtcgtcgccc tgtcgctgta ctggaagaac   360
gcctggtgca agtgaaaaat cggcgtcgcc aaaggtaaga acagcacga caagcgtacc   420
gacctgaaag atcgtgaatg ggcgctggac aaggcgcgta ttatgaagca cgccggacgt   480
taa                                                                  483
```

<210> SEQ ID NO 6
<211> LENGTH: 477
<212> TYPE: DNA
<213> ORGANISM: Acinetobacter baumannii

<400> SEQUENCE: 6

```
atggcgaaag caacagtagt aaagaaacat aatggcggaa ccatcgcaca aaacaaacgt    60
gcccgtcatg attattttat cgaagaaaaa tttgaagctg gcatgtcttt actaggctgg   120
```

```
gaagtaaaat ctttacgtgc cggtcgtatg agtttgacag aaagttatgt catttttaaa      180
aatggtgaag cattcttatt tggtgctcag attcaaccac tcctttctgc atctacacat      240
attgtgccgg aagctacacg tacacgaaaa ttattattat ctcgtcgtga acttgaaaag      300
cttatgggtg cggtgaacca aaaaggttat tcgtgcgttc cattagcatg ttactggaaa      360
ggtcatctgg ttaagcttga aattgcactc gtgaaggta aacaacttca cgataaacga       420
gcgactgaaa agaacgtga ctggcaacgt gataaagcac gtatatttca taagtaa         477
```

<210> SEQ ID NO 7  
<211> LENGTH: 480  
<212> TYPE: DNA  
<213> ORGANISM: Pseudomonas aeruginosa

<400> SEQUENCE: 7

```
atggctaagc agaagaaaca cccttcgggg accatcgcgc agaacaagaa ggctctgcac      60
gactatttca tcgaacaacg cttcgaggcg gcgtcgccc tggcgggctg ggaagtgaaa       120
agcctgcgcg ccggcaaggc ccagttggtc gacagctacg tgctgctcaa ggatggcgag      180
gcctggctgc tcggcagcca catcacgccc ctgaccaccg ccagcacgca cgtgatcgcc      240
gacccggtgc gcacgcgcaa gctgctgctg cacaagcgcg aactgggcaa gctgttcggc      300
gccgtgcaac agaagggcta cgcctgcgtc gctctgtcga tgtactggaa gaagcacctg      360
gtcaagtgcg agatcgccct ggccaagggc aagaaggact cgacaagcg ccacaccgag       420 aaggagcgcg actccgatcg ggagatccag cgcgccatgc cgacggcaa ggacgactga      480
```

<210> SEQ ID NO 8  
<211> LENGTH: 483  
<212> TYPE: DNA  
<213> ORGANISM: Enterobacter cloacae

<400> SEQUENCE: 8

```
atgacgaaga aaaaagcaca taaaccaggc tcggcgacca ttgcgctcaa caagcgtgct      60
cgccacgagt attttattga agaagaattc gaagctggcc ttgcattgca gggctgggaa      120
gtaaaatcgc tgcgcgccgg aaagccaat atcggtgata gttacgtgat cctgaaagat       180
ggcgaagcct tcctgttcgg tgccaacttc acgccgctga ccgtcgcctc gtcacactac      240
gtgtgtgacc caacgcgtac ccgtaagctg ctgttgaaca agcgcgaact ggagtccctt      300
tatgggcgca ttaaccgtga aggcttcacc gtggttgccc tgtcgctgta ctggaaaaat      360
gcctggtgca aagtgaaagt tggcgtcgcg aagggtaaaa aacagcacga caaacgtacc      420
gatctgaaag agcgcgaatg gcagctcgac aaaagcacgta ttatgaaaaa cgcaggacgt      480
tga                                                                    483
```

<210> SEQ ID NO 9  
<211> LENGTH: 483  
<212> TYPE: DNA  
<213> ORGANISM: Mycobacterium tuberculosis

<400> SEQUENCE: 9

```
gtgtccaagt cgtcgcgtgg cggccggcag atcgttgcca gcaatcgcaa agcccggcac       60
aactattcga tcatcgaggt gttcgaggcc ggggttgcgc tgcaaggcac ggaggtgaag      120
agcctgcggg aagggcaggc gtcgctggcc gattcgttcg ccaccatcga cgacggcgaa      180
gtgtggctgc gcaacgcgca catcccggaa taccggcacg gcagctggac caaccacgag      240
```

| | |
|---|---|
| ccgcgacgca accgcaaaact gctgttgcat cgccgccaga tcgacacctt ggtcggcaag | 300 |
| atccgcgaag gcaacttcgc cctggtgccg ttgtcgctgt atttcgccga aggcaaggtc | 360 |
| aaggttgagc ttgcgctggc ccgaggcaag caagcccgcg acaaacgcca ggacatggcc | 420 |
| cgtcgtgatg cccagcgtga agtgctccgc gagttgggtc ggcgcgctaa gggcatgacc | 480 |
| tga | 483 |

```
<210> SEQ ID NO 10
<211> LENGTH: 363
<212> TYPE: DNA
<213> ORGANISM: Escherichia coli

<400> SEQUENCE: 10
```

| | |
|---|---|
| ggggctgatt ctggattcga cgggatttgc gaaacccaag gtgcatgccg aggggcggtt | 60 |
| ggcctcgtaa aaagccgcaa aaaatagtcg caaacgacga aaactacgct ttagcagctt | 120 |
| aataacctgc ttagagccct ctctccctag cctccgctct taggacgggg atcaagagag | 180 |
| gtcaaaccca aaagagatcg cgtggaagcc ctgcctgggg ttgaagcgtt aaaacttaat | 240 |
| caggctagtt tgttagtggc gtgtccgtcc gcagctggca agcgaatgta aagactgact | 300 |
| aagcatgtag taccgaggat gtaggaattt cggacgcggg ttcaactccc gccagctcca | 360 |
| cca | 363 |

```
<210> SEQ ID NO 11
<211> LENGTH: 367
<212> TYPE: DNA
<213> ORGANISM: Enterococcus faecium

<400> SEQUENCE: 11
```

| | |
|---|---|
| ggggacgtta cggattcgac aggcacagtc gagcttgaat tgcgtttcgt aggttacgtc | 60 |
| tacgtaaaaa cgttacagtt aaatataact gctaaaaacg aaaacaactc ttacgcttta | 120 |
| gctgcctaaa aacagttagc gtagatcctc tcggcatcgc ccatgtgctc gagtaagggt | 180 |
| cctaacttta gtgggatacg tttcaacttt ccgtctgtaa gttgaaaaag agaacatcag | 240 |
| actagcgata cagaatgcct gtcactcggc aagctgtaaa gtgaatcctt aaatgagttg | 300 |
| actatgaacg tagatttta agtggcgatg tgtttggacg cgggttcgac tcccgccgtc | 360 |
| tccattg | 367 |

```
<210> SEQ ID NO 12
<211> LENGTH: 362
<212> TYPE: DNA
<213> ORGANISM: Staphylococcus aureus

<400> SEQUENCE: 12
```

| | |
|---|---|
| ggggacgttc atggattcga caggggtccc ccgagctcat taagcgtgtc ggagggttgt | 60 |
| cttcgtcatc aacacacaca gtttataata actggcaaat caaacaataa tttcgcagta | 120 |
| gctgcctaat cgcactctgc atcgcctaac agcatttcct atatgctgtt aacgcgattc | 180 |
| aaccttaata ggatatgcta aacactgccg tttgaagtct gtttagaaga aacttaatca | 240 |
| agctagcatc atgttggttg tttatcactt ttcatgatgc gaaacctttc gataaactac | 300 |
| acacgtagaa agatgtgtat caggacctct ggacgcgggt tcaaatcccg ccgtctccat | 360 |
| at | 362 |

```
<210> SEQ ID NO 13
<211> LENGTH: 363
```

```
<212> TYPE: DNA
<213> ORGANISM: Klebsiella pneumoniae

<400> SEQUENCE: 13
ggggctgatt ctggattcga cgggatttgc gaaacccaag gtgcatgccg aggggcggtt      60
ggcctcgtaa aaagccgcaa aaatagtcg caaacgacga aaactacgct ttagcagctt     120
aataacctgc tctgagccct ctctccctag cttccgctct aagacgggg atcaaagaga    180 ggtcaaaccc aaaagagatc gcgtggatgc cctgcctggg gttgaagcgt taaatctcat    240
caggctagtt tgttagtggc gtgtctgtcc gcagctggca agcgaatgta aagactgact    300
aagcatgtag tgccgaggat gtaggaattt cggacgcggg ttcaactccc gccagctcca    360
cca                                                                  363

<210> SEQ ID NO 14
<211> LENGTH: 360
<212> TYPE: DNA
<213> ORGANISM: Acinetobacter baumannii

<400> SEQUENCE: 14
ggggatgtta ttggcttcga cgccggtgat gaaactcata gatgcatgcc gagagcgcat     60
tttctctcgt aaataaaatt tgcatttaaa tagtcgcaaa cgacgaaact tacgctctag    120
ctgcctaagg gccgcttgtc cgcttcctag aatacttgtg gtctgggaac ccgactgaag    180
cgcacgcaca caagtccgta tagagtcaag cctcggggct ttataccaaa cttagaggat    240
cgcactttgt accctgttcg tcgggtcact tggtgttaaa acaatagacg atatctaagc    300
atgtagtatt ctcgagcgta gtgctggcgg acgcgggttc aactcccgcc atctccacca    360

<210> SEQ ID NO 15
<211> LENGTH: 353
<212> TYPE: DNA
<213> ORGANISM: Pseudomonas aeruginosa

<400> SEQUENCE: 15
ggggccgatt aggattcgac gccggtaaca aaacttgagg ggcatgccga gctggtagca     60
gaactcgtaa attcgctgct gcaaacttat agttgccaac gacgacaact acgctctagc    120
tgcttaatgc ggctagcagt cgctagggga tgcctgtaaa cccgaaacga ctgtcagata    180
gaacaggatc gccgccaagt tcgctgtaga cgtaacggct aaaactcata cagctcgctc    240
caagcaccct gccactcggg cggcgcggag ttaactcagt agagctggct aagcatgtag    300
aaccgatagc ggagagctgg cggacggggg ttcaaatccc cccggctcca cca           353

<210> SEQ ID NO 16
<211> LENGTH: 364
<212> TYPE: DNA
<213> ORGANISM: Enterobacter cloacae

<400> SEQUENCE: 16
ggggctgatt ctggattcga cgggatttgc gaaacccaag gtgcatgccg aggggcggtt     60
tgcctcgtaa aaagccgcaa aaaatagtc gcaaacgacg aaaactacgc tttagcagct    120
taataacctg ctctgagccc tctctcccta gcttccgctc ttaagacggg gattcaagag    180
aggtcaaacc caaaagagat cgcgtggaag ccctgcctgg ggttgaagcg ttaaaactaa    240
tcaggctagt acgttagtgg cgtgtttgtt cgcagctggc gtgcgaatgt aaagacaaac    300
taagcatgta gtaccgagga tgtagaaatt cggacgcggg ttcaactcc cgccagctcc    360
```

```
acca                                                                  364

<210> SEQ ID NO 17
<211> LENGTH: 368
<212> TYPE: DNA
<213> ORGANISM: Mycobacterium tuberculosis

<400> SEQUENCE: 17
ggggctgaac ggtttcgact tcgcgcatcg aatcaaggga agcgtgccgg tgcaggcaag      60
agaccaccgt aagcgtcgtt gcgaccaaat aagcgccgat tcacatcagc gcgactacgc    120
tctcgctgcc taagcgacgg ctagtctgtc agaccgggaa cgccctcggc ccggaccctg    180
gcatcagcta gagggatcca ccgatgagtc cggtcgcggg actcctcggg acaaccacag    240
cgactgggat cgtcatctcg gctagttcgc gtgaccggga gatccgagca gaggcatagc    300
gaactgcgca cggagaagcc ttgagggaat gccgtaggac ccgggttcga ttcccggcag    360
ctccaccg                                                             368

<210> SEQ ID NO 18
<211> LENGTH: 17
<212> TYPE: PRT
<213> ORGANISM: Artificial Sequence
<220> FEATURE:
<223> OTHER INFORMATION: Synthetic Sequence containing the conserved
      first alanine of the native tmRNA plus the sequence of the 16
      amino acids of the 11th domain of GFP

<400> SEQUENCE: 18

Ala Arg Asp His Met Val Leu His Glu Tyr Val Asn Ala Ala Gly Ile
1               5                   10                  15

Thr

<210> SEQ ID NO 19
<211> LENGTH: 54
<212> TYPE: DNA
<213> ORGANISM: Artificial Sequence
<220> FEATURE:
<223> OTHER INFORMATION: Synthetic Sequence encoding a peptide
      containing the conserved first alanine of the native tmRNA plus
      the sequence of the 16 amino acids of the GFP

<400> SEQUENCE: 19
gcacgtgacc acatggtcct tcatgagtac gtaaatgctg ctgggattac ataa            54

<210> SEQ ID NO 20
<211> LENGTH: 15
<212> TYPE: DNA
<213> ORGANISM: Artificial Sequence
<220> FEATURE:
<223> OTHER INFORMATION: Synthetic sequence which partially pairs with
      the sequence SEQ ID NO: 19 so as to form a helix

<400> SEQUENCE: 20
taacctaatc ctagc                                                      15

<210> SEQ ID NO 21
<211> LENGTH: 383
<212> TYPE: DNA
<213> ORGANISM: Artificial Sequence
<220> FEATURE:
<223> OTHER INFORMATION: Synthetic DNA Sequence encoding the tmRNA
      according to the invention in the case of Escherichia coli

<400> SEQUENCE: 21
```

-continued

```
gggggctgatt ctggattcga cgggatttgc gaaacccaag gtgcatgccg aggggcggtt    60
ggcctcgtaa aaagccgcaa aaaatagtcg cacgtgacca catggtcctt catgagtacg    120
taaatgctgc tgggattaca taataaccta atcctagccc tctctcccta gcctccgctc    180
ttaggacggg gatcaagaga ggtcaaaccc aaaagagatc gcgtggaagc cctgcctggg    240
gttgaagcgt taaaacttaa tcaggctagt ttgttagtgg cgtgtccgtc cgcagctggc    300
aagcgaatgt aaagactgac taagcatgta gtaccgagga tgtaggaatt tcggacgcgg    360
ttcaactccc gccagctcca cca                                           383
```

<210> SEQ ID NO 22
<211> LENGTH: 383
<212> TYPE: DNA
<213> ORGANISM: Artificial Sequence
<220> FEATURE:
<223> OTHER INFORMATION: Synthetic DNA Sequence encoding the tmRNA
      according to the invention in the case of Enterococcus faecium

<400> SEQUENCE: 22

```
ggggacgtta cggattcgac aggcacagtc gagcttgaat tgcgtttcgt aggttacgtc    60
tacgtaaaaa cgttacagtt aaatataact gcacgtgacc acatggtcct tcatgagtac    120
gtaaatgctg ctgggattac ataataacct aatcctagcg atcctctcgg catcgcccat    180
gtgctcgagt aagggtccta actttagtgg gatacgtttc aactttccgt ctgtaagttg    240
aaaaagagaa catcagacta gcgatacaga atgcctgtca ctcggcaagc tgtaaagtga    300
atccttaaat gagttgacta tgaacgtaga ttttaagtg gcgatgtgtt tggacgcggg    360
ttcgactccc gccgtctcca ttg                                           383
```

<210> SEQ ID NO 23
<211> LENGTH: 384
<212> TYPE: DNA
<213> ORGANISM: Artificial Sequence
<220> FEATURE:
<223> OTHER INFORMATION: Synthetic DNA Sequence encoding the tmRNA
      according to the invention in the case of Staphylococcus aureus

<400> SEQUENCE: 23

```
ggggacgttc atggattcga caggggtccc ccgagctcat taagcgtgtc ggagggttgt    60
cttcgtcatc aacacacaca gtttataata actgcacgtg accacatggt ccttcatgag    120
tacgtaaatg ctgctgggat tacataataa cctaatccta gcatcgccta acagcatttc    180
ctatatgctg ttaacgcgat tcaaccttaa taggatatgc taaacactgc cgtttgaagt    240
ctgtttagaa gaaacttaat caagctagca tcatgttggt tgtttatcac ttttcatgat    300
gcgaaacctt tcgataaact acacacgtag aaagatgtgt atcaggacct ctggacgcgg    360
gttcaaatcc cgccgtctcc atat                                          384
```

<210> SEQ ID NO 24
<211> LENGTH: 384
<212> TYPE: DNA
<213> ORGANISM: Artificial Sequence
<220> FEATURE:
<223> OTHER INFORMATION: Synthetic DNA Sequence encoding the tmRNA
      according to the invention in the case of Klebsiella pneumoniae

<400> SEQUENCE: 24

```
gggggctgatt ctggattcga cgggatttgc gaaacccaag gtgcatgccg aggggcggtt    60
ggcctcgtaa aaagccgcaa aaaatagtcg cacgtgacca catggtcctt catgagtacg    120
```

```
taaatgctgc tgggattaca ataaaccta atcctagccc tctctcccta gcttccgctc    180
ttaagacggg gatcaaagag aggtcaaacc caaaagagat cgcgtggatg ccctgcctgg    240
ggttgaagcg ttaaatctca tcaggctagt ttgttagtgg cgtgtctgtc cgcagctggc    300
aagcgaatgt aaagactgac taagcatgta gtgccgagga tgtaggaatt tcggacgcgg    360
gttcaactcc cgccagctcc acca                                          384
```

<210> SEQ ID NO 25
<211> LENGTH: 387
<212> TYPE: DNA
<213> ORGANISM: Artificial Sequence
<220> FEATURE:
<223> OTHER INFORMATION: Synthetic DNA Sequence encoding the tmRNA
      according to the invention in the case of Klebsiella pneumoniae

<400> SEQUENCE: 25

```
ggggatgtta ttggcttcga cgccggtgat gaaactcata gatgcatgcc gagagcgcat     60
tttctctcgt aaataaaatt tgcatttaaa tagtcgcacg tgaccacatg gtccttcatg    120
agtacgtaaa tgctgctggg attacataat aacctaatcc tagcgtccgc ttcctagaat    180
acttgtggtc tgggaacccg actgaagcgc acgcacacaa gtccgtatag agtcaagcct    240
cggggcttta taccaaactt agaggatcgc actttgtacc ctgttcgtcg ggtcacttgg    300
tgttaaaaca atagacgata tctaagcatg tagtattctc gagcgtagtg ctggcggacg    360
cgggttcaac tcccgccatc tccacca                                       387
```

<210> SEQ ID NO 26
<211> LENGTH: 380
<212> TYPE: DNA
<213> ORGANISM: Artificial Sequence
<220> FEATURE:
<223> OTHER INFORMATION: Synthetic DNA Sequence encoding the tmRNA
      according to the invention in the case of Pseudomonas aeruginosa

<400> SEQUENCE: 26

```
ggggccgatt aggattcgac gccggtaaca aaacttgagg ggcatgccga gctggtagca     60
gaactcgtaa attcgctgct gcaaacttat agttgcacgt gaccacatgg tccttcatga    120
gtacgtaaat gctgctggga ttacataata acctaatcct agccagtcgc tagggatgc    180 ctgtaaaccc gaaacgactg tcagatagaa caggatcgcc gccaagttcg ctgtagacgt    240
aacggctaaa actcatacag ctcgctccaa gcaccctgcc actcgggcgg cgcggagtta    300
actcagtaga gctggctaag catgtagaac cgatagcgga gagctggcgg acggggggttc    360 aaatcccccc ggctccacca                                               380
```

<210> SEQ ID NO 27
<211> LENGTH: 385
<212> TYPE: DNA
<213> ORGANISM: Artificial Sequence
<220> FEATURE:
<223> OTHER INFORMATION: Synthetic DNA Sequence encoding the tmRNA
      according to the invention in the case of Enterobacter cloacae

<400> SEQUENCE: 27

```
ggggctgatt ctggattcga cgggatttgc gaaacccaag gtgcatgccg aggggcggtt     60
tgcctcgtaa aaagccgcaa aaaaatagtc gcacgtgacc acatggtcct tcatgagtac    120
gtaaatgctg ctgggattac ataataacct aatcctagcc ctctctccct agcttccgct    180
cttaagacgg ggattcaaga gaggtcaaac ccaaaagaga tcgcgtggaa gccctgcctg    240
```

```
ggggttgaagc gttaaaacta atcaggctag tacgttagtg gcgtgtttgt tcgcagctgg      300
cgtgcgaatg taaagacaaa ctaagcatgt agtaccgagg atgtagaaat ttcggacgcg      360
ggttcaactc ccgccagctc cacca                                             385
```

```
<210> SEQ ID NO 28
<211> LENGTH: 385
<212> TYPE: DNA
<213> ORGANISM: Artificial Sequence
<220> FEATURE:
<223> OTHER INFORMATION: Synthetic DNA Sequence encoding the tmRNA
      according to the invention in the case of Mycobacterium
      tuberculosis

<400> SEQUENCE: 28
ggggctgaac ggtttcgact tcgcgcatcg aatcaaggga agcgtgccgg tgcaggcaag       60
agaccaccgt aagcgtcgtt gcgaccaaat aagcgcacgt gaccacatgg tccttcatga     120
gtacgtaaat gctgctggga ttacataata acctaatcct agctgtcaga ccgggaacgc     180
cctcggcccg gaccctggca tcagctagag ggatccaccg atgagtccgg tcgcgggact     240
cctcgggaca accacagcga ctgggatcgt catctcggct agttcgcgtg accgggagat     300
ccgagcagag gcatagcgaa ctgcgcacgg agaagccttg agggaatgcc gtaggacccg     360
ggttcgattc ccggcagctc caccg                                             385
```

```
<210> SEQ ID NO 29
<211> LENGTH: 26
<212> TYPE: DNA
<213> ORGANISM: Artificial Sequence
<220> FEATURE:
<223> OTHER INFORMATION: Synthetic anti-ARNtmRNA oligonucleotide

<400> SEQUENCE: 29
gctgctaaag cgtagttttc gtcgtt                                            26
```

```
<210> SEQ ID NO 30
<211> LENGTH: 10
<212> TYPE: PRT
<213> ORGANISM: Escherichia coli

<400> SEQUENCE: 30

Ala Asn Asp Glu Asn Tyr Ala Leu Ala Ala
1               5                   10
```

```
<210> SEQ ID NO 31
<211> LENGTH: 139
<212> TYPE: DNA
<213> ORGANISM: Artificial Sequence
<220> FEATURE:
<223> OTHER INFORMATION: Synthetic primer GFP11helix_forward

<400> SEQUENCE: 31
acccaaggtg catgccgagg ggcggttggc ctcgtaaaaa gccgcaaaaa atagtcgcac       60
gtgaccacat ggtccttcat gagtacgtaa atgctgctgg gattacataa taacctaatc    120 ctagcccctct ctccctagc                                                    139
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic primer GFP11helix_reverse
```

<400> SEQUENCE: 32
tagaatactc aagcttcgcg                                              20

<210> SEQ ID NO 33
<211> LENGTH: 31
<212> TYPE: DNA
<213> ORGANISM: Artificial Sequence
<220> FEATURE:
<223> OTHER INFORMATION: Synthetic primer tmGFP11_BstNav_forward

<400> SEQUENCE: 33
aaaagaattc ggggctgatt ctggattcga c                                 31

<210> SEQ ID NO 34
<211> LENGTH: 31
<212> TYPE: DNA
<213> ORGANISM: Artificial Sequence
<220> FEATURE:
<223> OTHER INFORMATION: Synthetic primer tmGFP11_BstNav_reverse

<400> SEQUENCE: 34
aaggctgcag tggtggagct ggcgggagtt g                                 31

<210> SEQ ID NO 35
<211> LENGTH: 42
<212> TYPE: DNA
<213> ORGANISM: Artificial Sequence
<220> FEATURE:
<223> OTHER INFORMATION: Synthetic primer pUC19_tm11_forward

<400> SEQUENCE: 35
ggaagcttaa tacgactcac tatagggggct gattctggat tc                    42

<210> SEQ ID NO 36
<211> LENGTH: 32
<212> TYPE: DNA
<213> ORGANISM: Artificial Sequence
<220> FEATURE:
<223> OTHER INFORMATION: Synthetic primer pUC19_tm11_reverse

<400> SEQUENCE: 36
ggggatcccg tctcctggtg gagctggcgg ga                                32

<210> SEQ ID NO 37
<211> LENGTH: 23
<212> TYPE: DNA
<213> ORGANISM: Artificial Sequence
<220> FEATURE:
<223> OTHER INFORMATION: Synthetic primer GFPfold_for

<400> SEQUENCE: 37
ctcgatcccg cgaaattaat acg                                          23

<210> SEQ ID NO 38
<211> LENGTH: 20
<212> TYPE: DNA
<213> ORGANISM: Artificial Sequence
<220> FEATURE:
<223> OTHER INFORMATION: Synthetic primer GFP1-10nonSTOP_rev

<400> SEQUENCE: 38
cttttcgttg ggatctttcg                                              20

<210> SEQ ID NO 39
<211> LENGTH: 88

```
<212> TYPE: DNA
<213> ORGANISM: Artificial Sequence
<220> FEATURE:
<223> OTHER INFORMATION: Synthetic primer alaGFPfold_rev

<400> SEQUENCE: 39
ccggcctagg ttatgtaatc ccagcagcat ttacgtactc atgaaggacc atgtggtcac    60
gtgccttttc gttgggatct ttcgaaag                                       88

<210> SEQ ID NO 40
<211> LENGTH: 20
<212> TYPE: DNA
<213> ORGANISM: Artificial Sequence
<220> FEATURE:
<223> OTHER INFORMATION: Synthetic primer smpB_forward

<400> SEQUENCE: 40
tcacgacgca tatgacgaag                                                20

<210> SEQ ID NO 41
<211> LENGTH: 21
<212> TYPE: DNA
<213> ORGANISM: Artificial Sequence
<220> FEATURE:
<223> OTHER INFORMATION: Synthetic primer smpB_reverse

<400> SEQUENCE: 41
tcgagacggt gggcgttttt c                                              21

<210> SEQ ID NO 42
<211> LENGTH: 41
<212> TYPE: DNA
<213> ORGANISM: Artificial Sequence
<220> FEATURE:
<223> OTHER INFORMATION: Synthetic anti-ssrAGFP11 oligonucleotide

<400> SEQUENCE: 42
cccagcagca tttacgtact catgaaggac catgtggtca c                        41

<210> SEQ ID NO 43
<211> LENGTH: 822
<212> TYPE: DNA
<213> ORGANISM: Artificial Sequence
<220> FEATURE:
<223> OTHER INFORMATION: Synthetic Sequence of the PCR product PCR (SEQ
      ID NO: 43 above) to produce the superfolder GFP with a
      supplementary alanine

<400> SEQUENCE: 43
ctcgatcccg cgaaattaat acgactcact atagggggaat tgtgagcgga taacaattcc    60
cctctagaaa taattttgtt taactttaag aaggagatat acatatgggt ggcactagta   120
gcaaaggaga agaacttttc actggagttg tcccaattct tgttgaatta gatggtgatg   180
ttaatgggca caattttct gtcagaggag agggtgaagg tgatgctaca atcggaaaac   240
tcacccttaa atttatttgc actactggaa aactacctgt tccatggcca acacttgtca   300
ctactctgac ctatggtgtt caatgctttt cccgttatcc ggatcacatg aaaaggcatg   360 acttttcaa gagtgccatg cccgaaggtt atgtacagga acgcactata tctttcaaag   420
atgacgggaa atacaagacg cgtgctgtag tcaagtttga aggtgatacc cttgttaatc   480
gtatcgagtt aaagggtact gattttaaag aagatggaaa cattctcgga cacaaactcg   540
agtacaactt taactcacac aatgtataca tcacggcaga caaacaaaag aatggaatca   600
```

| | | | | | |
|---|---|---|---|---|---|
| aagctaactt | cacagttcgc | cacaacgttg | aagatggttc | cgttcaacta | gcagaccatt | 660 |
| atcaacaaaa | tactccaatt | ggcgatggcc | ctgtcctttt | accagacaac | cattacctgt | 720 |
| cgacacaaac | tgtcctttcg | aaagatccca | acgaaaaggc | acgtgaccac | atggtccttc | 780 |
| atgagtacgt | aaatgctgct | gggattacat | aacctaggcc | gg | | 822 |

The invention claimed is:

1. A reporter system for the trans-translational activity of a bacterial species selected from the group consisting of *Escherichia coli*, *Enterococcus faecium*, *Staphylococcus aureus*, *Klebsiella pneumoniae*, *Acinetobacter baumannii*, *Pseudomonas aeruginosa*, *Enterobacter cloacae*, and *Mycobacterium tuberculosis*, comprising:
 a nucleotide sequence encoding the first 10 domains of GFP and not comprising a stop codon;
 a nucleotide sequence encoding the SmpB protein of said bacterial species; and
 a modified tmRNA, wherein the modified tmRNA is the tmRNA of said bacterial species, in which the portion of sequence encoding the proteolysis tag is replaced with a nucleotide sequence consisting of sequence SEQ ID NO: 19 which encodes the 11$^{th}$ domain of GFP of sequence SEQ NO: 18.

2. The reporter system according to claim 1, wherein the GFP is Superfolder GFP.

3. The reporter system according to claim 1, wherein the nucleotide sequence encoding the first 10 domains of GFP and not comprising a stop codon is a DNA sequence of which the transcription produces an mRNA encoding the first 10 domains of GFP and not comprising a stop codon.

4. The reporter system according to claim 1, wherein the nucleotide sequence encoding the first 10 domains of GFP and not comprising a stop codon is functionally linked, in the 3' position, to the sequence of a strong terminator.

5. The reporter system according to claim 4, wherein the strong terminator is a succession of rare codons, a ribonuclease recognition system, a ribosome-blocking sequence, or a terminator comprising at least one stem-loop structure.

6. The reporter system according to claim 1, wherein the nucleotide sequence encoding the first 10 domains of GFP and not comprising a stop codon is functionally linked, in the 5' position, to a translation initiation site corresponding to a ribosome-binding site and to a promoter.

7. The reporter system according to claim 6, wherein the promoter is the T7 promoter and wherein the nucleotide sequence encoding the first 10 domains of GFP and not comprising a stop codon and functionally linked, in the 5' position, to a translation initiation site corresponding to an RBS ribosome-binding site and to the T7 promoter consists of the sequence SEQ ID NO: 1.

8. The reporter system according to claim 1, wherein:
 the bacterial species is *Escherichia coli* and the nucleotide sequence encoding the SmpB protein is the sequence SEQ ID NO: 2 or any variant encoding the SmpB protein of *Escherichia coli*;
 the bacterial species is *Enterococcus faecium* and the nucleotide sequence encoding the SmpB protein is the sequence SEQ ID NO: 3 or any variant encoding the SmpB protein of *Enterococcus faecium*;
 the bacterial species is *Staphylococcus aureus* and the nucleotide sequence encoding the SmpB protein is the sequence SEQ ID NO: 4 or any variant encoding the SmpB protein of *Staphylococcus aureus*;
 the bacterial species is *Klebsiella pneumoniae* and the nucleotide sequence encoding the SmpB protein is the sequence SEQ ID NO: 5 or any variant encoding the SmpB protein of *Klebsiella pneumoniae*;
 the bacterial species is *Acinetobacter baumannii* and the nucleotide sequence encoding the SmpB protein is the sequence SEQ ID NO: 6 or any variant encoding the SmpB protein of *Acinetobacter baumannii*;
 the bacterial species is *Pseudomonas aeruginosa* and the nucleotide sequence encoding the SmpB protein is the sequence SEQ ID NO: 7 or any variant encoding the SmpB protein of *Pseudomonas aeruginosa*;
 the bacterial species is *Enterobacter cloacae* and the nucleotide sequence encoding the SmpB protein is the sequence SEQ ID NO: 8 or any variant encoding the SmpB protein of *Enterobacter cloacae*; or
 the bacterial species is *Mycobacterium tuberculosis* and the nucleotide sequence encoding the SmpB protein is the sequence SEQ ID NO: 9 or any variant encoding the SmpB protein of *Mycobacterium tuberculosis*.

9. The reporter system according to claim 1, wherein the modified tmRNA is further modified such that the sequence 3' of the sequence encoding the 11$^{th}$ domain of GFP is replaced with a sequence which pairs with a region of the sequence encoding the 11$^{th}$ domain of GFP so as to form a helix.

10. The reporter system according to claim 9, wherein the sequence which pairs with a region of the sequence encoding the 11$^{th}$ domain of GFP so as to form a helix is a nucleotide sequence consisting of the sequence SEQ ID NO: 20.

11. The reporter system according to claim 10, wherein:
 the bacterial species is *Escherichia coli* and the nucleotide sequence encoding the modified tmRNA is the sequence SEQ ID NO: 21;
 the bacterial species is *Enterococcus faecium* and the nucleotide sequence encoding the modified tmRNA is the sequence SEQ ID NO: 22;
 the bacterial species is *Staphylococcus aureus* and the nucleotide sequence encoding the modified tmRNA is the sequence SEQ ID NO: 23;
 the bacterial species is *Klebsiella pneumoniae* and the nucleotide sequence encoding the modified tmRNA is the sequence SEQ ID NO: 24;
 the bacterial species is *Acinetobacter baumannii* and the nucleotide sequence encoding the modified tmRNA is the sequence SEQ ID NO: 25;
 the bacterial species is *Pseudomonas aeruginosa* and the nucleotide sequence encoding the modified tmRNA is the sequence SEQ ID NO: 26;
 the bacterial species is *Enterobacter cloacae* and the nucleotide sequence encoding the modified tmRNA is the sequence SEQ ID NO: 27; or
 the bacterial species is *Mycobacterium tuberculosis* and the nucleotide sequence encoding the modified tmRNA is the sequence SEQ ID NO: 28.

12. The reporter system according to claim 1, wherein at least one of the following sequences: the nucleotide sequence encoding the first 10 domains of GFP and not comprising a stop codon; the nucleotide sequence encoding the SmpB protein; and the nucleotide sequence encoding the modified tmRNA, is inserted into a plasmid.

13. The reporter system according to claim 1, wherein the nucleotide sequence encoding the first 10 domains of GFP and not comprising a stop codon, the nucleotide sequence encoding the SmpB protein; and the nucleotide sequence encoding the modified tmRNA, are inserted into one or more plasmids.

14. The reporter system according to claim 1, further comprising:
an anti-tmRNA oligonucleotide which comprises, or consists of, a nucleotide sequence complementary to the nucleotide sequence encoding the proteolysis tag of the tmRNA of the bacterial species of the bacterial system for protein synthesis with which the reporter system is intended to be used.

15. A method for screening for compounds capable of inhibiting bacterial trans-translation, comprising steps of:
(a) incubating a bacterial system for protein synthesis with a test compound;
(b) adding, to the bacterial system for protein synthesis incubated with the test compound, a reporter system for trans-translation according to claim 1; and
(c) identifying the effect of the test compound on trans-translation by detecting and/or by measuring GFP fluorescence.

16. The screening method according to claim 15, further comprising a step of:
(d) comparing the measurement of the fluorescence measured in step (c) with the measurement of the fluorescence measured under the same conditions in the absence of the test compound.

17. The screening method according to claim 16, wherein the test compound is identified as a compound capable of inhibiting bacterial trans-translation if the fluorescence measured in step (d) is greater than the fluorescence measured in step (c).

18. The screening method according to claim 15, wherein the bacterial system for protein synthesis is from the same bacterial species as the bacterial species of the reporter system for trans-translational activity.

19. The screening method according to claim 15, wherein the bacterial system for protein synthesis is from a bacterial species different than the bacterial species of the reporter system for trans-translational activity.

20. The screening method according to claim 15, wherein the bacterial system for protein synthesis is an in vitro system.

21. The screening method according to claim 20, wherein the bacterial system for protein synthesis in vitro is a reconstituted cell-free protein synthesis system.

22. The screening method according to claim 20, wherein the reconstituted cell-free protein synthesis system comprises:
a bacterial ribosome,
tRNAs of the bacterial species,
elements required for transcription by the bacterial ribosome,
elements required for translation by the bacterial ribosome,
an energy regenerating system, and
buffers, and salts.

23. The screening method according to claim 15, wherein the bacterial system for protein synthesis is an in vivo system.

24. The screening method according to claim 23, wherein the in vivo bacterial system for protein synthesis is a bacterial cell.

25. The screening method according to claim 24, wherein (1) the in vivo bacterial system for protein synthesis is a host bacterial cell comprising, integrated into its genome, the nucleotide sequence encoding the SmpB protein and the nucleotide sequence encoding the modified tmRNA and (2) in step (b), only the nucleotide sequence encoding the first 10 domains of GFP and not comprising a stop codon is added to the host bacterial cell.

26. A kit comprising a reporter system for the trans-translational activity of a bacterial species according to claim 1.

27. The kit according to claim 26, further comprising instructions for carrying out a screening method as claimed in claim 15.

28. The kit according to claim 27, further comprising a bacterial system of a protein synthesis as defined in claim 18.

* * * * *